(12) United States Patent
Andre-Fontaine et al.

(10) Patent No.: US 7,635,480 B2
(45) Date of Patent: Dec. 22, 2009

(54) PEPTIDES FOR PREVENTING, DIAGNOSING AND TREATING ANIMAL AND/OR HUMAN LEPTOSPIROSIS

(75) Inventors: Geneviève Andre-Fontaine, Nort sur Erdre (FR); Benoît Chatrenet, Nice (FR); Christine Branger, Vertou (FR); André Aubert, Antibes (FR)

(73) Assignee: Virbac S.A. (FR)

(*) Notice: Subject to any disclaimer, the term of this patent is extended or adjusted under 35 U.S.C. 154(b) by 107 days.

(21) Appl. No.: 10/533,193

(22) PCT Filed: Oct. 24, 2003

(86) PCT No.: PCT/FR03/03154

§ 371 (c)(1),
(2), (4) Date: Sep. 29, 2005

(87) PCT Pub. No.: WO2004/041855

PCT Pub. Date: May 21, 2004

(65) Prior Publication Data

US 2007/0197432 A1    Aug. 23, 2007

(30) Foreign Application Priority Data

Oct. 30, 2002    (FR) .................................. 02 13585

(51) Int. Cl.
*A61K 39/02* (2006.01)
*C07K 14/20* (2006.01)

(52) U.S. Cl. .............................. 424/190.1; 424/197.11; 530/324; 530/350; 530/825

(58) Field of Classification Search ....................... None
See application file for complete search history.

(56) References Cited

U.S. PATENT DOCUMENTS

| 6,077,822 A * | 6/2000 | Dyrsting et al. ................. 514/8 |
| 2003/0124567 A1* | 7/2003 | Andre-Fontaine et al. ...... 435/6 |
| 2003/0186887 A1* | 10/2003 | Jones ........................... 514/13 |

FOREIGN PATENT DOCUMENTS

| WO | WO 96/36355 A | * | 11/1996 |
| WO | WO 99/42478 A | * | 8/1999 |
| WO | WO 01/59123 A | * | 8/2001 |

\* cited by examiner

Primary Examiner—Jeffrey E Russel

(57) ABSTRACT

The present invention provides a compound chosen from: a peptide represented by the sequence SEQ ID No: 1 below:

SEQ ID No: 1 Lys-Ala-Lys-Pro-Val-Gln-Lys-Leu-Asp-Asp-Asp-Asp-Asp-Gly-Asp-Asp-Thr-Tyr-Lys-Glu-Glu-Arg-His-Asn-Lys and homologs of this peptide exhibiting at least 80% similarity with the sequence SEQ ID No: 1 and comprising from 20 to 30 amino acids. These compounds are useful in preventing, diagnosing and treating animal and/or human leptospirosis.

7 Claims, 13 Drawing Sheets

Survival curve for gerbils immunized with the PP peptide coupled to the KLH carrier protein and subjected to a *Leptospira interrogans* sl serovar canicola leptospiral challenge

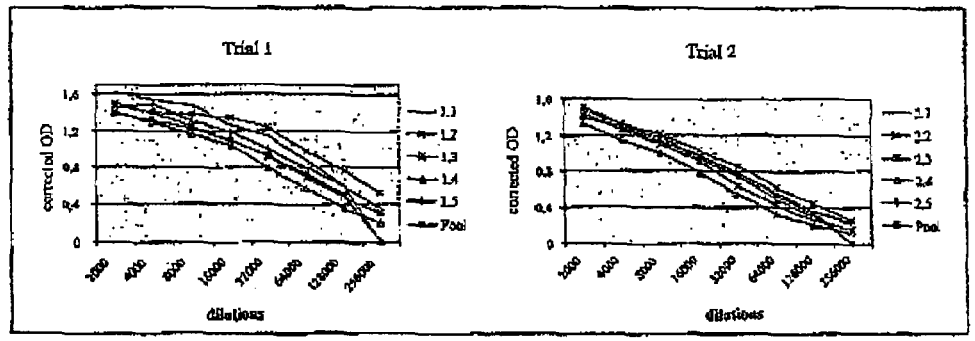

Figure 1: IgG$_1$ antibody response of 5 mice immunized with the PP peptide coupled to the KLH carrier protein for trial 1 and 2, expressed as corrected optical density as a function of dilution

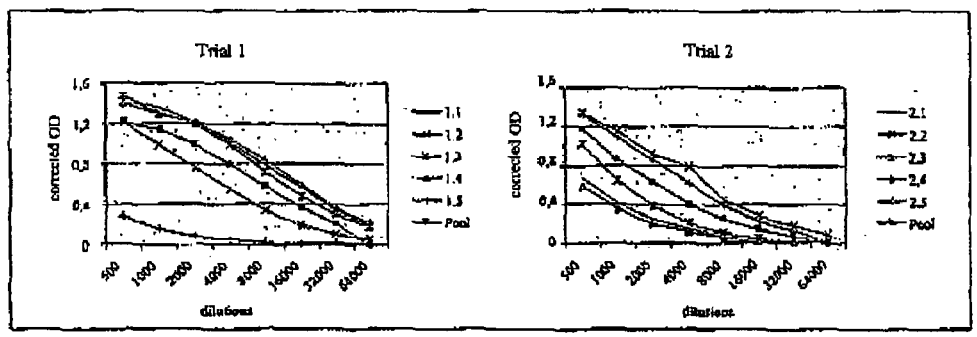

Figure 2: IgG$_{2A}$ antibody response of 5 mice immunized with the PP peptide coupled to the KLH carrier protein for trial 1 and 2, expressed as corrected optical density as a function of dilution

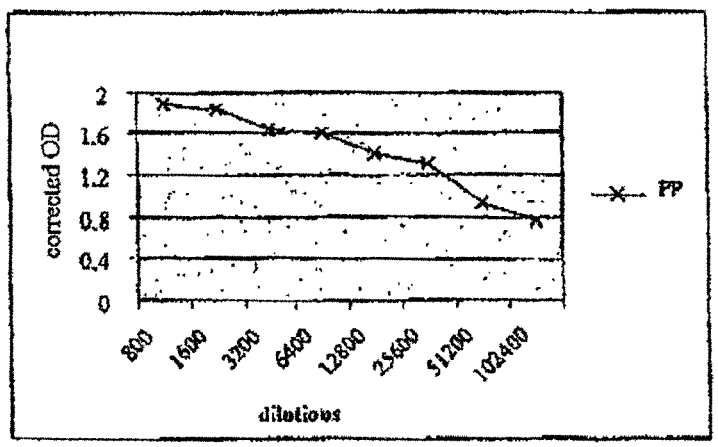

Figure 3: IgG antibody response of a rabbit immunized with the PP peptide, expressed as corrected optical density as a function of dilution

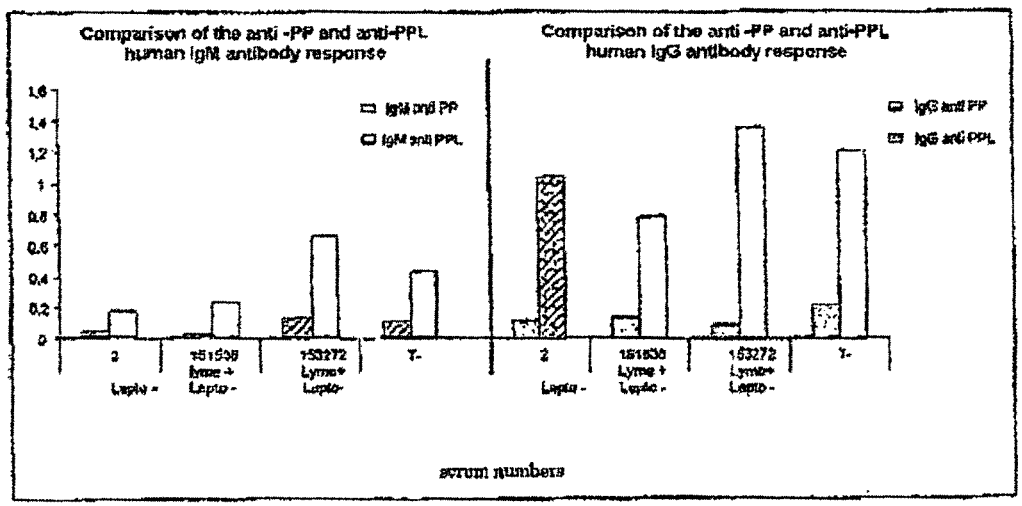

Figure 4: Comparison of the IgM and IgG antibody response, in sera originating from human patients not suffering from leptospirosis (confirmed by the MAT) but two of whom are suffering from Lyme disease (serum 151358 and 153272), against the PP peptide and against the recombinant PPL protein, expressed as optical density (OD)

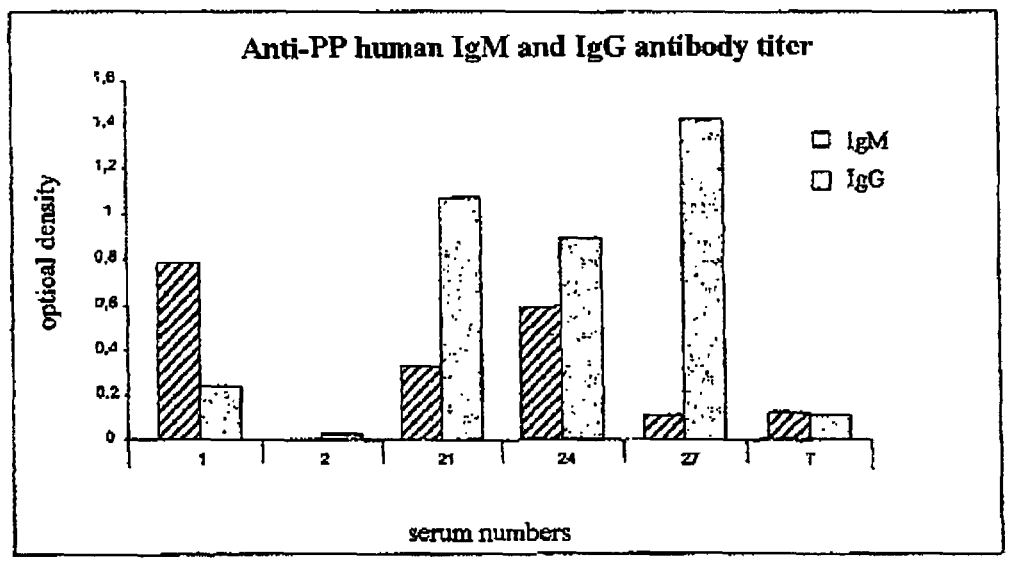

Figure 5: IgM and IgG antibody response, in 5 sera originating from human patients suffering from leptospirosis confirmed or not confirmed by the MAT, against the PP peptide expressed as optical density (OD)

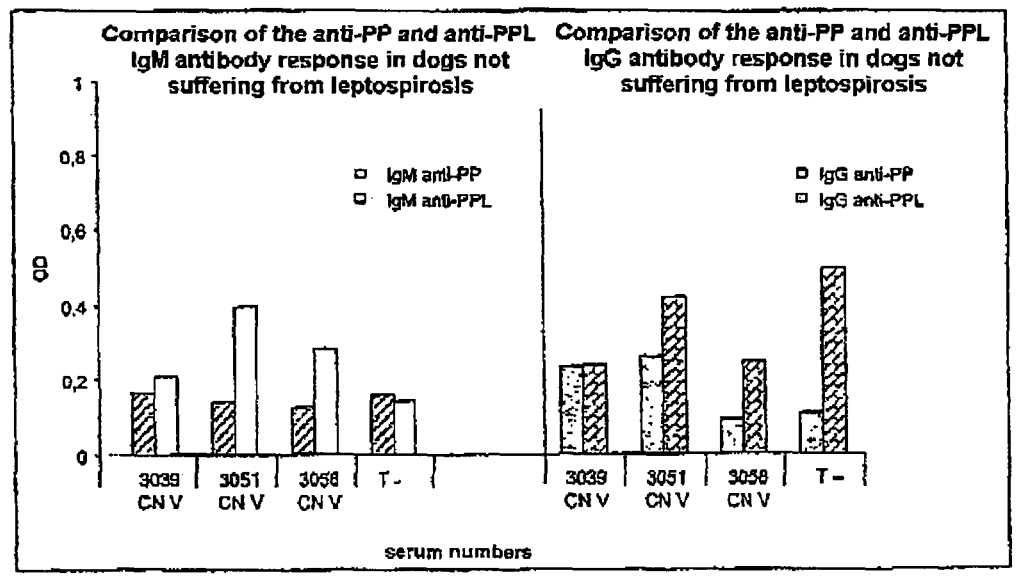

Figure 6: Compared PP and PPL response, either IgM or IgG, for sera originating from 4 SPF dogs, three of which are immunized against leptospirosis (CN V), expressed as optical density (OD)

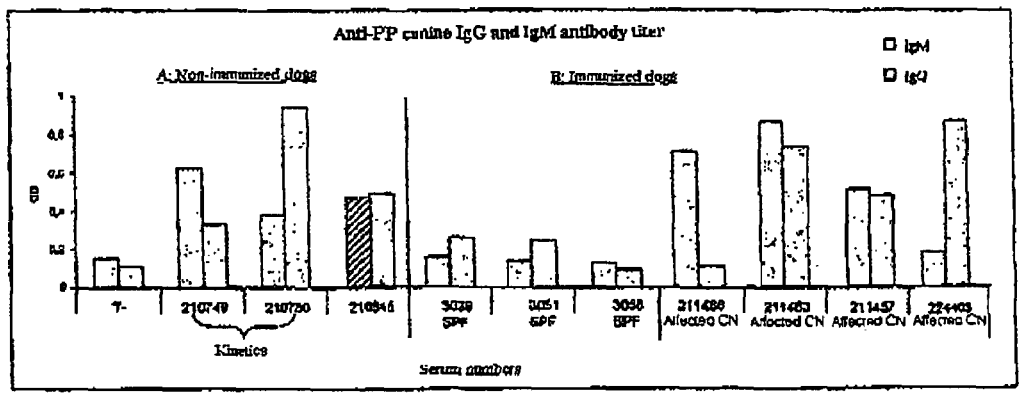

Figure 7: IgM and IgG antibody response, in 7 sera originating from dogs that are clinical suspects (leptospirosis confirmed by the MAT), compared with that of 3 immunized normal SPF dogs (3039, 3051, 3058), against the PP peptide, expressed as optical density (OD); Nos. 210749 and 210750 originate from the same animal, taken 4 days apart (CN = dog)

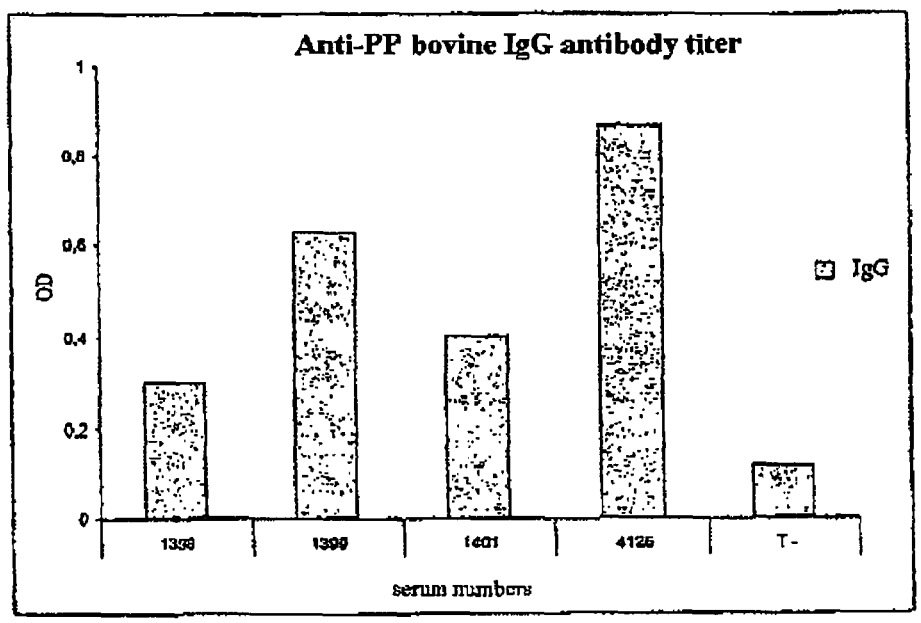

Figure 8: IgG antibody response, in 4 bovine sera derived from herds suspected to be suffering from leptospirosis, against the PP peptide, expressed as optical density

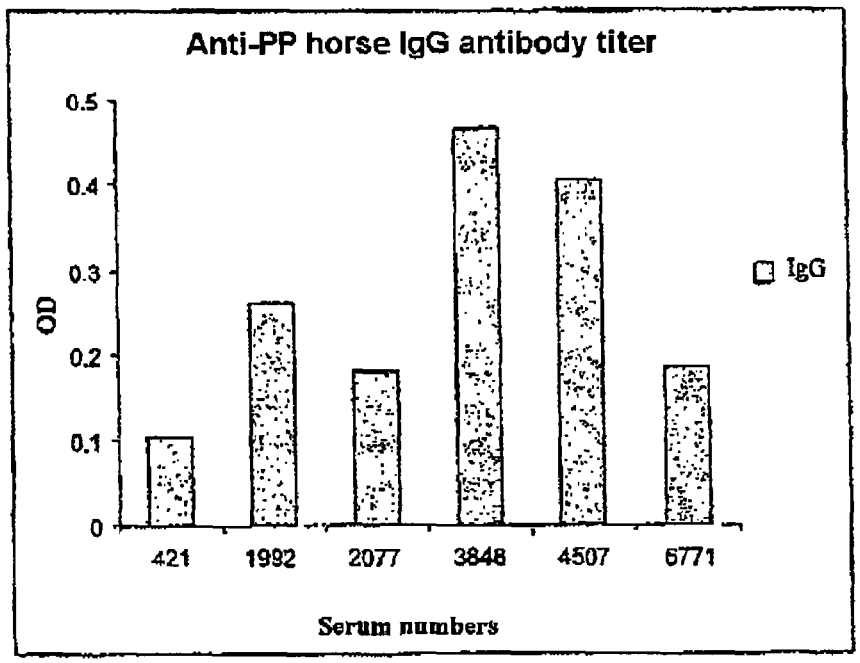
Figure 9: IgG antibody response, in 6 equine sera, against the PP peptide, expressed as optical density
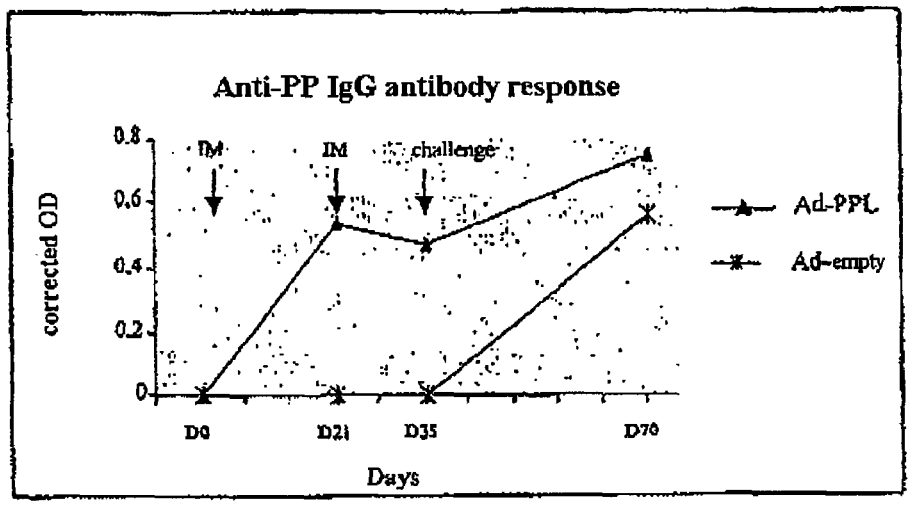
Figure 10: Kinetics of the antibody response against the PP peptide, expressed as corrected optical density, of gerbils subjected to adenovirus-mediated immunization

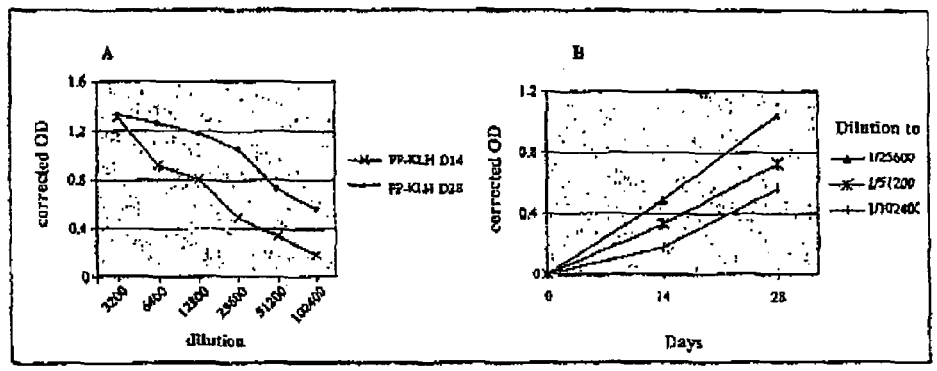

Figure 11: Kinetics of the IgG antibody response against the PP peptide, expressed as corrected optical density as a function of dilution (A) or of time (B), of gerbils immunized with the PP peptide coupled to the KLH carrier protein

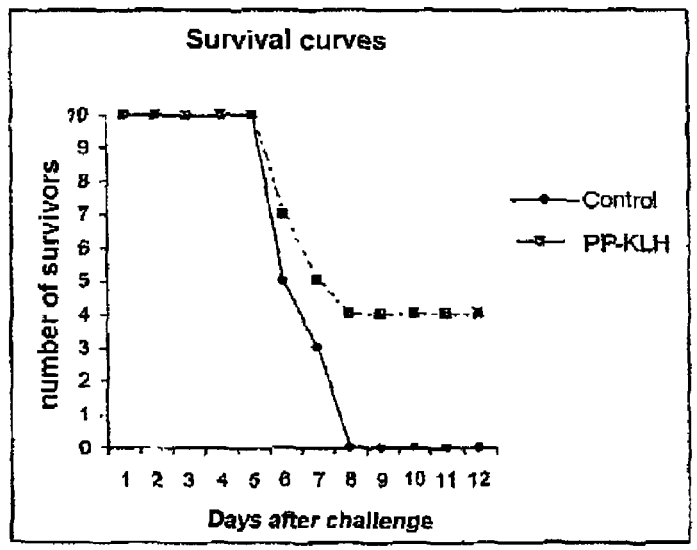

Figure 12: Survival curve for gerbils immunized with the PP peptide coupled to the KLH carrier protein and subjected to a Leptospira interrogans sl serovar canicola leptospiral challenge

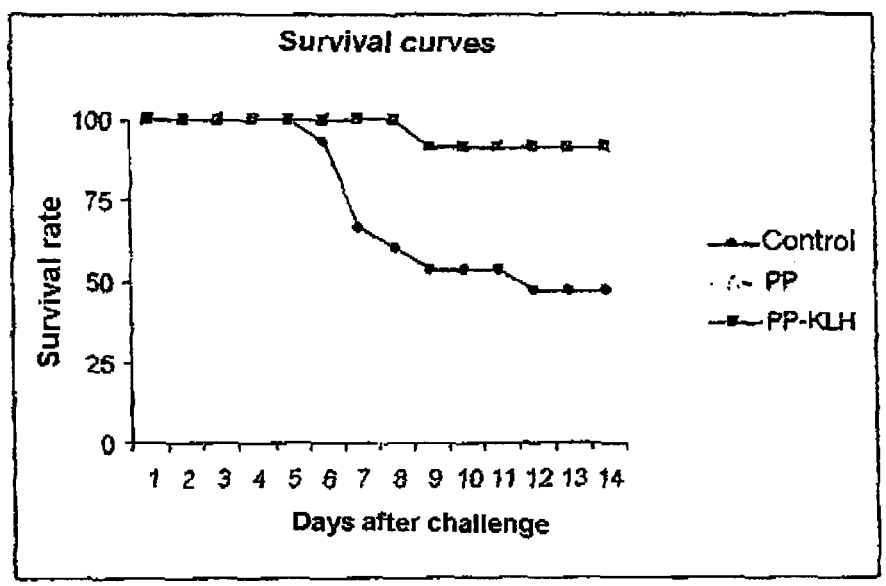
Figure 13: Survival curve for gerbils immunized with PP-KLH or PP and subjected to a *Leptospira interrogans* sl serovar canicola leptospiral challenge Figure 14: Timetable for the immunization trial with the PP peptide coupled to the KLH carrier protein in dogs, with a *Leptospira interrogans sl* serovar canicola leptospiral challenge

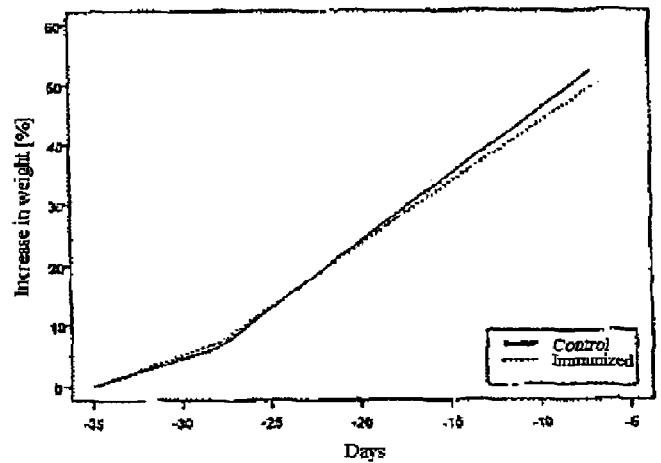

Figure 15: Evolution of the increase in weight of the control dogs and immunized dogs (immunized with the PP peptide coupled to the KLH carrier protein) before challenge

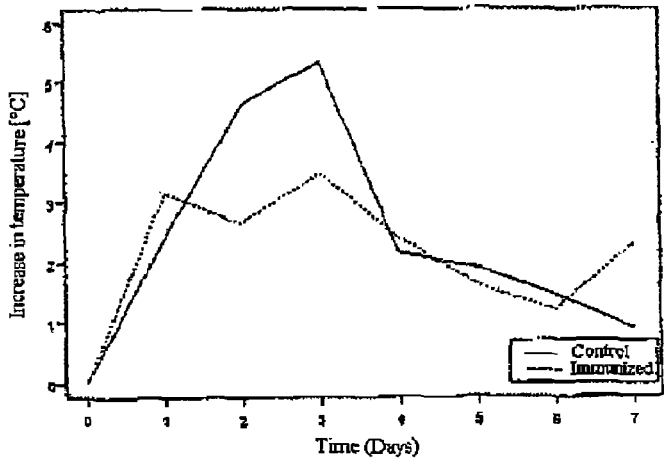

Figure 16: Evolution of the increase in temperature of the control dogs and immunized dogs (immunized with the PP peptide coupled to the KLH carrier protein) subjected to a *Leptospira interrogans sl* serovar canicola leptospiral challenge

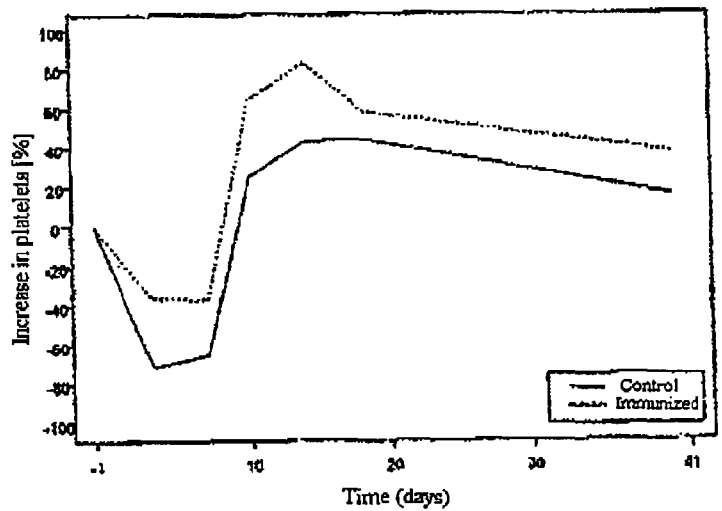

Figure 17: Evolution in the variation in platelets of control dogs and immunized dogs (immunized with the PP peptide coupled to the KLH carrier protein) subjected to a *Leptospira interrogans sl* serovar canicola leptospiral challenge

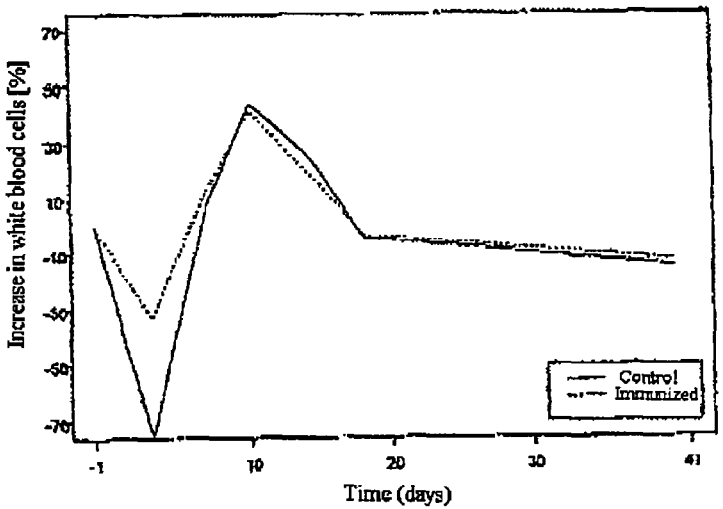

Figure 18: Quantitative evolution of the variation in white blood cells of control dogs and immunized dogs (immunized with the PP peptide coupled to the KLH carrier protein) subjected to a *Leptospira interrogans sl* serovar canicola leptospiral challenge

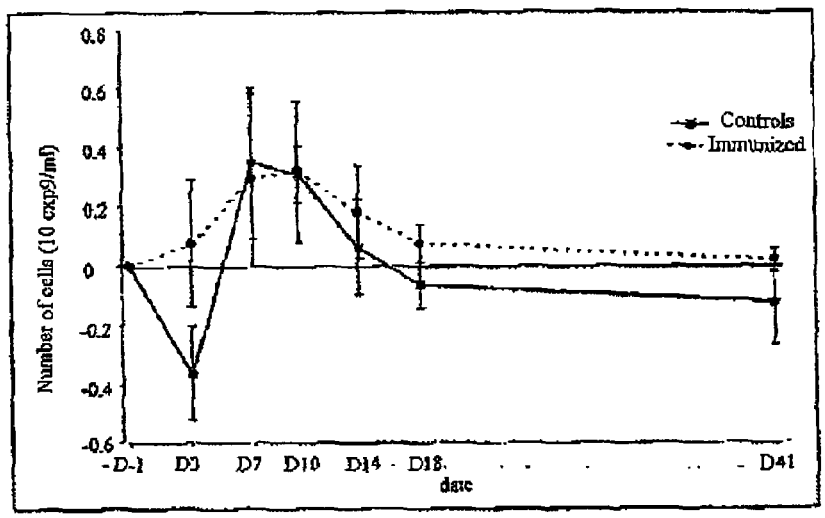

Figure 19: Quantitative evolution of the variation in lymphocytes of control dogs and immunized dogs (immunized with the PP peptide coupled to the KLH carrier protein) subjected to a Leptospira interrogans sl serovar canicola leptospiral challenge

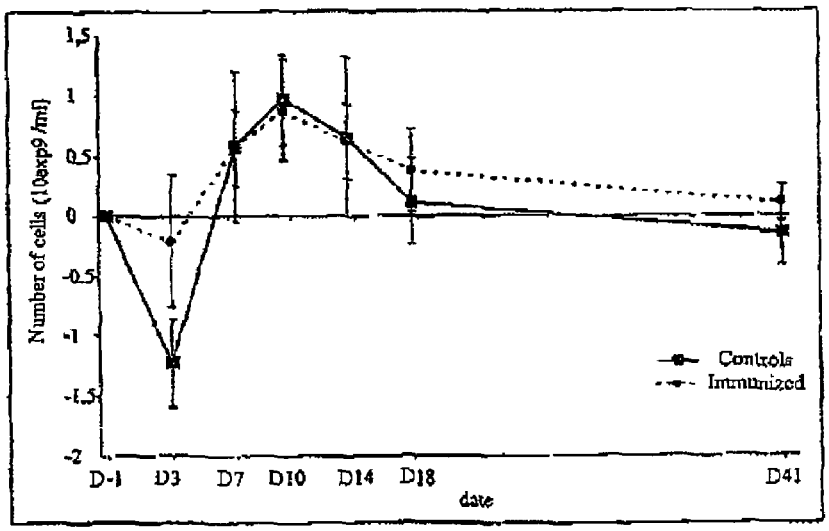

Figure 20: Quantitative evolution of the variation in monocytes of control dogs and immunized dogs (immunized with the PP peptide coupled to the KLH carrier protein) subjected to a Leptospira interrogans sl serovar canicola leptospiral challenge

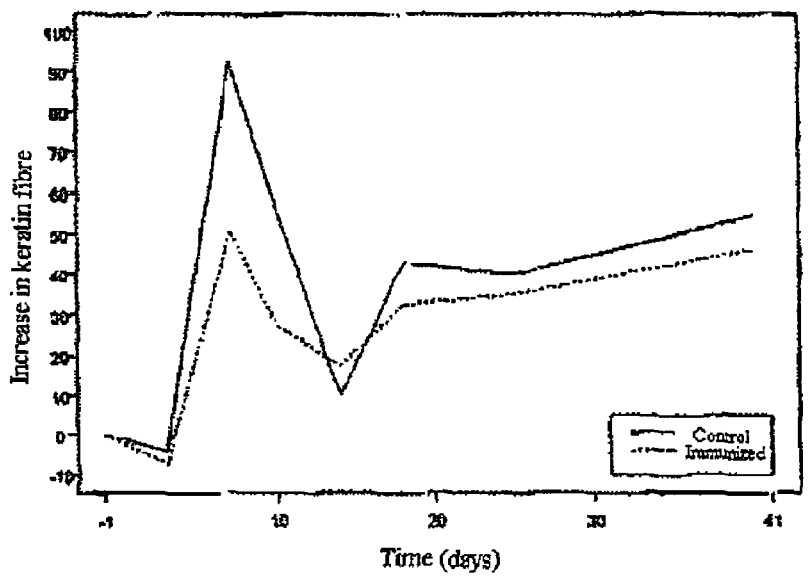

Figure 21: Evolution of the increase in creatinine of the control dogs and immunized dogs (immunized with the PP peptide coupled to the KLH carrier protein) subjected to a *Leptospira interrogans* sl serovar canicola leptospiral challenge

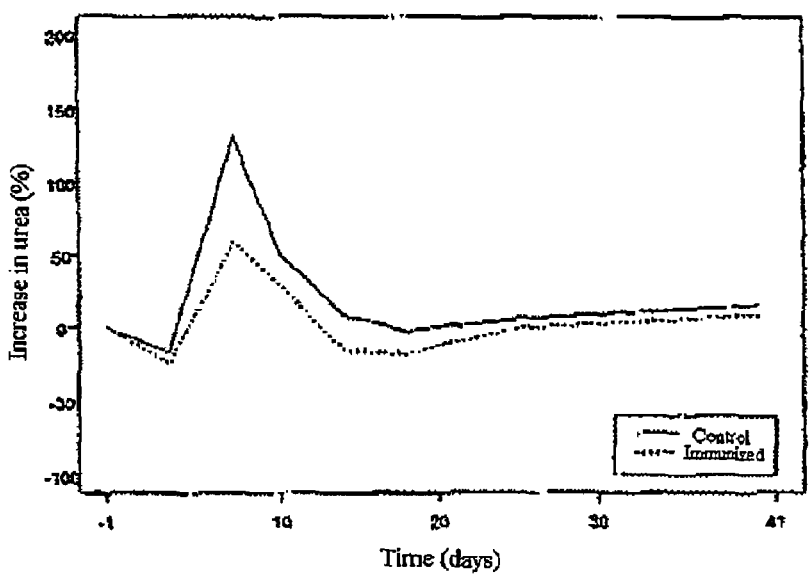

Figure 22: Evolution of the increase in urea of control dogs and immunized dogs (immunized with the PP peptide coupled to the KLH carrier protein) subjected to a *Leptospira interrogans* sl serovar canicola leptospiral challenge

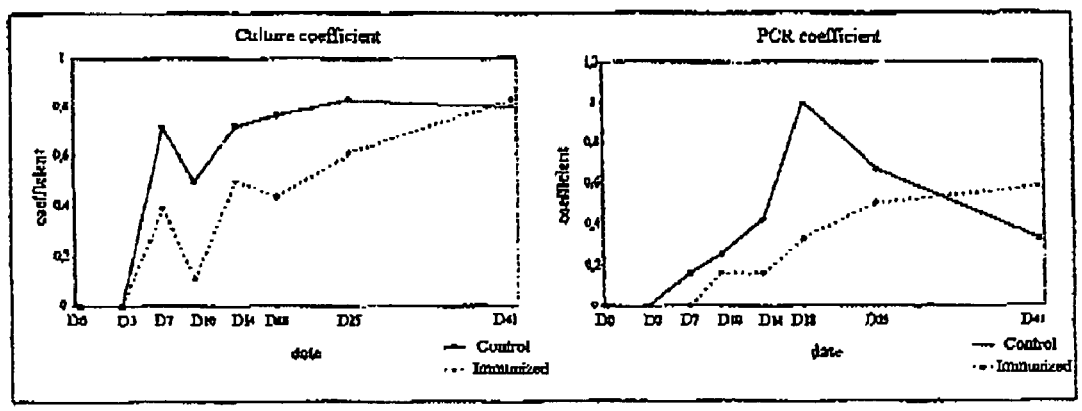
Figure 23: Evolution of the cumulative coefficient obtained for the cultures and PCR of the batches of control dogs and immunized dogs (immunized with the PP peptide coupled to the KLH carrier protein) subjected to a Leptospira interrogans sl serovar canicola leptospiral challenge

PEPTIDES FOR PREVENTING, DIAGNOSING AND TREATING ANIMAL AND/OR HUMAN LEPTOSPIROSIS

The present invention relates to peptides capable of inducing protection against leptospiroses (in particular by immunization), and to immunogenic compositions (diagnostic and/or therapeutic reagents) comprising one or more of these peptides or the antibodies, nucleic acids or vectors that are derived therefrom. These compositions are particularly advantageous since they make it possible to induce an immune response or protection against various pathogenic strains, in particular against several different pathogenic serogroups of leptospires, and to provide a diagnosis common to all clinical cases whatever the species affected.

Pathogenic leptospires are responsible for infectious diseases affecting humans and animals. Leptospiroses are part of the zoonoses monitored by the WHO because of their worldwide distribution and the seriousness of the disease (fatal in 2 to 20% of patients depending on how early diagnosis and treatment are). In animals, the economical impact is considerable, the disease being responsible for reproductive problems in farm animals (ruminants or pigs) or for serious clinical signs that impair the health of pets, namely dogs, or that of animals in sport, namely horses.

The importance of leptospiroses is illustrated in particular by virtue of two aspects: first of all, their impact on public health (hospitalizations, inabilities to work, sometimes death, use of immunizations in the context of protection against occupational diseases in certain countries, including France), secondly their economical impact (cost of implementation of public health programs, loss of production for farm animals and cost of vaccines used in many countries for combating this decrease in production, emotional loss of pets and/or cost of vaccines currently available in dogs in virtually all countries in the world, and also financial loss due to the impairment of sporting performances of horses).

It is particularly difficult to combat these infections, given the bacteriological complexity of these microorganisms and the diversity of the reservoirs constituted by animals of the wild fauna, that carry, excrete and disseminate these microorganisms in their urine. The bacteriological complexity of these bacteria is such that two classifications for these microorganisms currently coexist: a serological classification and a genomic classification.

According to the serological classification, all the pathogenic strains have been classified in the same pathogenic species *Leptospira interrogans* s.l., as opposed to the saprophytic aquaculture strains classified in *Leptospira biflexa* s.l. The species *Leptospira interrogans* is divided up into more than 25 different serogroups, each of these serogroups itself being composed of several serovars exhibiting, among one another, antigenic groups that are sufficient for them to be grouped together. Some 220 different serovars can thus be counted for the pathogenic species. This classification is made on the basis of the agglutinating antibody-inducing antigens; for this reason, it is still the only one used in the context of serological diagnosis of the infection.

According to the genomic classification, based on the study of genetic homologies, the pathogenic species *Leptospira interrogans* sl has been broken up into different species referred to as genomospecies: *Leptospira interrogans* sensu stricto (s.s.), *Leptospira kirshneri, L. borgpetersenii, L. weilii, L. noguchii, L. santarosai, L. meyeri, L. fainei*, etc.

The clinical expression of leptospirosis is very polymorphic, according to the infecting strains, but also to the species.

Thus, humans sensitive to leptospirosis generally develop rapidly evolving acute forms with the liver, kidneys or lungs being affected. The earliness of diagnosis generally conditions the effectiveness of the antibiotic treatment. The French vaccine directed against *Icterohaemorrhagiae* provides protection only against this serogroup that is considered to be the most pathogenic.

In dogs, the most sensitive animal species, immunization against the two serogroups considered to be dominant in this species (*Icterohaemorrhagiae* and *Canicola*) has been used. However, the vaccine only protects against these two serogroups and does not make it possible to prevent infection with a wild-type strain belonging to another serogroup. This explains the development of chronic disorders, that are still poorly identified by veterinary practitioners who consider that a dog immunized against "leptospirosis" cannot develop a chronic form related to infection with a wild-type strain.

In horses, which are greatly at risk due to the conditions under which they are kept, rare acute forms, but also uncharacteristic forms such as drops in form and substandard sporting performances, appear. Some abortions in this species are also related to leptospirosis infection. Finally, a recurring eye condition is attributed to the consequences of infection with leptospires. This condition, which compromises the animal's future due to the blindness that it may cause, is moreover included in France on the list of latent defects.

In ruminants and pigs, leptospirosis is essentially expressed through reproductive disorders, comprising either abortions or infertility, these being disorders for which the economic weight may be estimated as being sufficiently great for certain countries to set up large-scale immunization and/or eradication steps.

Given the importance and the diversity of the pathological forms, any suspicion of leptospirosis, whether it is an individual clinical case or a breeding stock problem, is generally the subject of experimental confirmation methods. Diagnosis (and screening) in two parts may thus be necessary, depending on the duration of progression of the disease. In acute cases, direct demonstration of the microorganism is essential. In chronic cases, indirect demonstration via the serological response is generally sufficient in terms of diagnosis, but, in a second step, recognition of animals that are carrying microorganisms, and are therefore excreters, requires demonstration of the microorganism.

Currently, the direct demonstration of the pathogenic agent of the microorganism can be carried out essentially by two methods: isolation and PCR.

Bacteriological isolation is a very laborious method. The natural fragility of leptospires means that only samples treated within a limited period of time allow the possible isolation of a leptospiral strain. It should be noted that the probability of isolating a leptospire is generally low, given the requirements of these microorganisms; in addition, it may take several weeks to obtain a response, given the slowness with which the cultures develop.

PCR has therefore proved to be a much more advantageous tool in terms of diagnosis. However, this method is currently only developed in humans, for whom it is carried out using a blood sample taken from the patient in the acute phase. Performing PCR as a diagnostic method on tissues such as products from abortion is still only at the experimental stage. As regards the screening for animals that excrete leptospires by analyzing urine, which method would be useful in animal rearing, it is not currently operational.

Serological diagnosis of the microorganism, consisting in demonstrating antibodies that reveal an infection, is generally carried out using the microagglutination test (MAT), which is currently the reference method. The drawbacks of this method are related to the bacteriological heterogeneity of leptospires. The method requires the use of live microorganisms (the culturing of which is delicate) and is, moreover, based on demonstrating agglutinating antibodies induced by the surface antigens of leptospires, which antigens were used to classify the leptospires and therefore express the heterogeneity of these bacteria. This means that the use of serological diagnosis requires the patient's serum to be brought into contact with a live strain representative of each of the different serogroups, thereby multiplying the manipulations for the same serum.

In terms of protection, it has always been considered in the prior art that only whole bacteria are capable of providing protective antigens and, moreover, that no cross protection exists between different serogroups. This means that, currently, the vaccines that are commercially available are made up of a suspension, or more precisely of an addition of suspensions, of bacteria representative of each of the serogroups necessary for protecting the species for which the vaccine is intended. Given the great diversity of the serogroups, a choice must be made according to the species and the epidemiological conditions. Thus, the normal vaccines used in dogs combine a suspension of inactivated bacteria of the *Icterohaemorrhagiae* serogroup and one of the *Canicola* serogroup. Vaccines used in pigs and ruminants in the USA combine suspensions of serovars belonging to the serogroups: *Icterohaemorrhagiae, Pomona, Grippotyphosa, Canicola* and *Sejroë* (hardjo serovar) for example. The vaccine for human use sold in France at the current time comprises the *Icterohaemorrhagiae* serogroup, etc.

The problem with these vaccine preparations is their failure in terms of complete protection against leptospirosis. An immunized individual for whom the immunization is maintained according to the methods prescribed by the vaccine producers is protected against the infection and/or the disease induced by a wild-type strain belonging only to the serogroups present in the vaccine. Protection is therefore only provided (and, even so, this protection may be incomplete) against infection with one or more given serogroups, represented in the vaccine preparation.

However, in previous studies (Gitton X, André-Fontaine G. André F, Ganière JP. "Immunoblotting study of the antigenic relationships among eight serogroups of *Leptospira*". *Vet Microbiol* 1992; 32:293-303), we determined antigens common to all pathogenic leptospires, capable of inducing cross protection between several serogroups, according to the following approach.

Thus, in a first step, it has been demonstrated that the presence of whole bacterial bodies is not essential for the induction of homologous protection. The expression "homologous response or protection" is intended to mean the protection induced by a preparation consisting of the leptospires belonging to the same serogroup as the leptospires used in the challenge performed by a sensitive laboratory animal and making it possible to assess the effectiveness and the authenticity of the conferred protection. This was demonstrated by immunizing animals with a total leptospiral extract obtained by rupturing the bacteria. In a second step, it has been demonstrated that total extracts of various serogroups make it possible to induce heterologous protection within the species *L. interrogans* sl. Reference is made to heterologous protection when the challenge is performed with a strain that does not belong to the serogroup used for the immunization. This was demonstrated by immunizations carried out with total extracts of cultures of the serogroups *Autumnalis, Canicola* or *Icterohaemorrhagiae*, followed by challenges using *Icterohaemorrhagiae* or *Canicola* strains, the virulence of which is maintained in the laboratory. The third step consists in demonstrating that the antigen(s) responsible for this cross protection is (are) absent from, or express very little by, the saprophyte species: a total extract of *L. biflexa* did not make it possible to protect animals against a challenge. The fourth step consists in identifying the antigens that differentiate the pathogenic species from the saprophyte species. For this: comparisons of electrophoretic profiles or of immunoblots of total extracts of leptospires of various pathogenic or non-pathogenic serogroups were carried out and show antigenic bands that overlap from 14 to 200 kD, 24 of which are common to the pathogenic species, and in particular the zone 21-26 kD, which is serogroup-specific (Gitton X, André-Fontaine G, AndréF, Ganière J-P. "Immunoblotting study of the antigenic relationships among eight serogroups of *Leptospira*". *Vet Microbiol* 1992; 32:293-303). Immunoblots of total extracts recognized by serum from infected dogs were carried out: this made it possible to show that the zone 21-31 kD, and more particularly 25-31, 32-34 and 45 kD, would be associated with belonging to the pathogenic species; the antigenic zone differentiating the pathogenic species from the saprophyte species was therefore located between 21 and 45 kD (Gitton X, Buggin-Daubié M, AndréF, Ganière J-P, André-Fontaine G, "Recognition of *Leptospira interrogans* antigens by vaccinated or infected dogs". *Vet Microbiol* 1994; 4:87-97). However, the use of a total extract allows the protein antigens to migrate, but also the lipopolysaccharide antigens. Now, the prior art defines the latter as being responsible for the protection against leptospirosis. The fifth step therefore had to assess the possible respective role, in the cross protection, of the lipopolysaccharide antigens and of the protein antigens prepared separately. This fifth step defined the nature of the antigen(s) responsible for this cross protection. Purified lipopolysaccharide (LPS) extracts were prepared by the Westphall method of extracting with phenol-water under hot conditions. This preparation method makes it possible to obtain the lipopolysaccharide (LPS) fraction in pure form. The residue extract contains the proteins (simple or complex), but also the residue LPS. We have demonstrated that the pure LPS extract is responsible for a powerful protective, but exclusively homologous, effect. This clearly confirms the prior data regarding the lack of cross protection between serogroups. In fact, the LPS corresponds to the outer antigenic structures responsible for the production of agglutinating antibodies used as a basis for serological classification, but also responsible for the protective effect of the vaccine preparations. According to the prior art, it was therefore necessary for a vaccine to be capable of inducing the production of agglutinating antibodies at significant rates in order to protect an animal against an infection with a homologous leptospire. The sixth step consisted in monitoring the ability of a protein extract of an *Autumnalis* or *Canicola* strain, purified of any trace of LPS, to induce homologous protection in the same way as the purified LPS, but also to induce protection against a heterologous challenge observed during the previous trials with total extracts. This was carried out by immunization with a protein extract obtained by chloroform/methanol extraction performed on the interface of a phenol/water extraction which had allowed the prior purification of LPS, followed by a homologous or heterologous challenge depending on the case (Sonrier C, Branger C, Michel V, Ruvoen-Clouet N, Ganiere J P, Andre-Fontaine G. "Evidence of cross-protection within *Leptospira interrogans* in an experimental model" *Vaccine* 2000 Aug. 15; 19(1):86-94). In the seventh step, it was possible, using the Biorad Prep-cell, to separate various proteins segregating in this range, in order to carry out the sequencing thereof. Three bands were subjected to the sequencing study, a protein of 32 kD and two proteins of 34 kD. The NH$_2$-terminal sequences were defined, along with an internal sequence of about twelve amino acids corresponding to the major peak (peak 14) obtained by HPLC. The 32 kD protein was designated PPL. In an eighth step, degenerate nucleotide probes were constructed, the PPL gene was cloned, and the production of recombinant PPL protein was carried out and enabled the production of monoclonal antibodies. The PPL gene was inserted into a nonreplicative human adenovirus and effective protection against challenges carried out on gerbils was observed after administration of these recombinant viruses, in particular as vaccines (Branger C, Sonrier C, Chatrenet B, Klonjkowski B, Ruvoen-Clouet N, Aubert A, Andre-Fontaine G, Eloit M, "Identification of the hemolysis-associated protein 1 as a cross-protective immunogen of *Leptospira interrogans* by adenovirus-mediated vaccination" *Infect Immun.* 2001 November; 69(11):6831-8).

However, the recombinant protein produced by a prokaryotic system does not make it possible to provide significant protection against the various pathogenic leptospiral strains.

Moreover, the serological diagnosis of leptospiroses by means of the microagglutination test is late and does not allow early detection of the disease. It is not rare for an animal to die from leptospirosis before the latter is diagnosed.

Document WO 01/59123 describes the identification of a 32 kD protein, designated PPL, comprising a sequence TFLPYGSVINYYGYVK (referenced herein as SEQ ID NO:2), this protein being common to certain pathogenic strains of leptospirosis. The PPL sequence comprises 272 amino acids. That document indicates that its subject is PPL fragments, but it does not describe any of them in particular. The sequence of this PPL protein integrated into an adenoviral vector showed a heterologous protective effect.

Document WO 99/42478 describes a membrane protein LipL32 which is present in certain pathogenic leptospiral strains. This protein comprises 272 amino acids. It can be used to induce an immune response directed against certain leptospiral strains.

However, it is in no way envisaged, in that document, that this protein makes it possible to induce heterologous protection against various leptospiral strains.

Document WO 96/36355 describes two membrane proteins of pathogenic leptospiral strains, LipL1 and LipL2, having a weight of 35 kDa and 41 kDa, respectively. These proteins are used to produce an immune response against certain leptospiral strains.

However, it is in no way envisaged, in that document, that this protein makes it possible to induce heterologous protection against various leptospiral strains.

The inventors therefore set themselves the aim of identifying peptides capable of inducing effective protection against the various pathogenic leptospiral strains, it being possible for this protection to be induced directly, without involving the expression of these peptides in an adenovirus.

The inventors also set themselves the aim of developing a method for the early detection of infection with the various pathogenic leptospiral strains in order to allow diagnosis of leptospirosis at a stage of the infection where administering a treatment to the individual is effective.

The present invention at present makes it possible to solve the drawbacks of the various methods of immunization, screening, diagnosis and treatment described in the prior art. The present invention in fact describes the identification of an antigenic leptospiral unit: the PP peptide, common to multiple leptospiral serogroups, in particular pathogenic leptospiral serogroups. The present invention also allows the production of polypeptides, peptides and antibodies that can be used either in vaccine, approaches or in therapeutic approaches that are effective and capable of inducing protection against multiple pathogenic leptospiral serovars. The present invention also makes it possible to carry out tests for detecting or screening for the pathogenic leptospires themselves, or the infection that they bring about, not restricted to specific serovars. The present invention also makes it possible to carry out detection tests that are simpler than the MAT methods described in the prior art, since they do not require microorganisms to be cultured. The present invention also describes nucleic acids, vectors, probes, primers and also recombinant cells that can be used for producing polypeptides, peptides or proteins or for detecting leptospires or their products in any biological test sample (for example, biological fluids such as blood, plasma, urine, milk, cerebrospinal fluid, tissue, organ, cell culture, etc.) or test sample of other origin (for instance a sample soiled by biological materials, such as river water, stagnant water, drinking water, stored water used by companies such as slate quarries, market gardeners, etc.).

The first subject of the invention is a peptide called PP, which is a fragment of a 32 kDa protein PPL described in international application WO 01/59123. This PP peptide consists of 25 amino acids and is represented by the sequence SEQ ID No: 1 represented below:

SEQ ID No: 1 Lys-Ala-Lys-Pro-Val-Gln-Lys-Leu-Asp-Asp-Asp-Asp-Asp-Gly-Asp-Asp-Thr-Tyr-Lys-Glu-Glu-Arg-His-Asn-Lys

The sequence SEQ ID No: 1 and, more generally, the compounds of the present invention have unforeseeable advantages compared with the proteins of the prior art:
  obtaining of protection against the various pathogenic leptospiral strains using a single compound,
  obtaining an early diagnosis of leptospirosis,
  obtaining a discriminating (infection/vaccine) diagnosis of leptospirosis.

A subject of the invention is also homologs of the PP peptide, its pharmaceutically acceptable salts, its functional fragments, its chemical analogs and certain chemical derivatives of this peptide.

For the purpose of the present invention, the term "homologs" is intended to mean peptides whose amino acid sequence exhibits at least 60% similarity with the sequence SEQ ID No: 1, even more preferentially 70%, even more preferentially still 80%, preferably at least 90%, and even more favorably at least 95%, or better still 98%, similarity with the sequence SEQ ID No: 1.

The expression "X % similarity between a peptide P and the sequence SEQ ID No: 1" is intended to mean that, when the sequence of P is aligned opposite SEQ ID No: 1, in the same direction, X % of the amino acids of P are identical to the corresponding amino acid of SEQ ID No: 1 or are replaced with an amino acid of the same class, it being understood that, if the sequences are not of the same length, a space will optionally be placed between the amino acids of the sequence concerned. The degree of homology can be evaluated by methods well known to those skilled in the art (for example, WILBUR W. J. et al Proceedings of the National Academy of Sciences USA 80, 726-730 (1983); MYERS et al, *Comput. Appl. Biosci.* 4, 11-17 (1988)).

For the purpose of the present invention, the homology with SEQ ID No: 1 extends to peptides comprising from 15 to 40 amino acids and whose sequence, once aligned with SEQ ID No: 1, with the spaces placed between the appropriate amino acids, has a similarity that is included in the values indicated above. Preferably, the homology extends to peptides comprising from 20 to 30 amino acids, even more preferably from 22 to 28 amino acids.

The expression "amino acids of the same class" is intended to mean an amino acid having substantially identical chemical properties.

In particular, this expression is intended to mean amino acids having substantially the same charge, and/or the same hydrophilicity or hydrophobicity, and/or the same aromaticity.

Such amino acid combinations generally include:

(i) glycine, alanine, valine, (ii) isoleucine, leucine, (iii) tryptophan, tyrosine, phenylalanine, (iv) aspartic acid, glutamic acid, (v) arginine, lysine, histidine, (vi) asparagine, glutamine, (vii) serine, threonine.

Other amino acid substitutions can be envisioned for the purpose of the present invention, in which substitutions an amino acid is replaced with another amino acid of the same class, i.e. having comparable properties, the substitution amino acid being a non-natural amino acid.

This is the case, for example, of the enantiomers and diastereoisomers of natural amino acids, hydroxyproline, norleucine, ornithine, citrulline, cyclohexylalanine, of β-amino acids such as 3-amino-propionic acid, and of Ω-amino acids such as 4-amino-butyric acid. Such amino acids are well known to those skilled in the art and can be prepared by known methods. Also included in the present invention are the substitutions of one or more amino acids with a non-natural amino acid carrying a group for detection of the peptide, such as an amino acid carrying a fluorescent or photoactivable group or a radiolabeled amino acid.

A particular example of a homolog consists of the functional fragments of the peptides according to the invention; these are peptides corresponding to one of the sequences according to the invention, in which one or more amino acids are removed from the sequence but which conserve an immunogenic activity comparable to that described for the PP peptide, in particular a comparable antibody titer. The preferred functional fragments of the peptides according to the invention are those for which at most six amino acids, more preferably 4 amino acids, more preferably still 2 amino acids, are removed; even more preferably, those for which one amino acid is removed.

Usually, substitutions of amino acids of the same class make it possible for the peptide to conserve its immunogenic activity. Suitable substitutions may be determined by testing the antimicrobial properties of the peptides obtained, using activity assays such as those described below. The invention relates more specifically to molecules that induce an antibody titer and/or confer protection comparable to those that can be obtained using the PP peptide.

According to the invention, the term "salts" relates both to the amine salts of a carboxyl function of the peptide chain and to the acid addition salts of an amine group of this same polypeptide chain. The salts of a carboxyl function can be formed with an inorganic or organic base. The inorganic salts include, for example, alkali metal salts such as sodium salts, potassium salts and lithium salts; alkaline earth metal salts such as, for example: calcium salts, barium salts and magnesium salts; ammonium salts, ferrous salts, ferric salts, zinc salts, manganese salts, aluminum salts, magnesium salts.

These salts with organic &mines include those formed, for example, with trimethylamine, triethylamine, tri(n-propyl) amine, dicyclohexylamine, triethanolamine, arginine, lysine, histidine, ethylenediamine, glucosamine, methylglucamine, purines, piperazines, piperidines, caffeine and procaine.

The acid addition salts include, for example, the salts with inorganic acids such as, for example, hydrochloric acid, hydrobromic acid, sulfuric acid, phosphoric acid, nitric acid; the salts with organic acids such as, for example, acetic acid, oxalic acid, tartaric acid, succinic acid, maleic acid, fumaric acid, gluconic acid, citric acid, malic acid, ascorbic acid, benzoic acid.

Chemical derivatives of the peptides according to the invention include alpha-amino peptide compounds, and substituted N-alpha acyl derivatives of the form RCO—, in which R represents an alkyl, alkenyl, alkynyl, aryl or aralkyl group, that is linear, branched or cyclic, comprising from 1 to 50, preferably from 1 to 8, carbon atoms. The preferred N-alpha acyl group is the acetyl group. Such amine-terminal substituents can increase the activity of the peptide by slowing down or by preventing enzymatic degradation of the peptides in vivo.

Other chemical derivatives of the peptides according to the invention include derivatives substituted on the C-terminal acid function with a group chosen from —$NH_2$, and alkyloxy, alkylthio or alkylamino of the form —OR, —SR or —NHR, in which R, can represent an alkyl, alkenyl, alkynyl or aryl chain or an aralkyl group, that is linear, branched or cyclic, comprising from 1 to 50, preferably from 8 to 50, carbon atoms.

Another type of chemical derivative of the peptides according to the invention includes derivatives carrying a pharmacophore substituent, such as a fluorescent group, a photoactivable group, a radiolabeled group or any other group for the spectroscopic detection and quantitative evaluation of the peptide according to the invention in a biological sample without degradation of the biological sample.

Preferably, according to the invention, the amino acids that make up the peptides are L enantiomers. However, one or more amino acids of the peptide sequence can be replaced with its D enantiomer.

By way of the chemical analogs, in the peptides according to the invention, one or more amide peptide linkages (—CO—NH—) can be replaced with an isosteric linkage such as: —$CH_2NH$—, $CH_2S$—, —$CH_2CH_2$—, —CH=CH— (cis and trans), —$COCH_2$, —$CH(OH)CH_2$— and —$CH_2SO$—. This substitution can be carried out by methods well known to those skilled in the art (reference may, for example, be made to: SPATOLA, Vega Data, Vol. 1, issue 3 (1983); SPATOLA, Chemistry and Biochemistry of Amino Acids Peptides and Proteins, Weinstein, ed., Marcel Dekker, New York, p. 267 (1983). MORLEY J.-S., Trends Pharm. Sci., 463-468 (1980); HUDSON et al, Int. J. Pept. Prot. Res. 14, 177-185 (1979); SPATOLA et al, Life Sci., 38, 1243-1249 (1986); Hann, J. Chem. Soc. Perkin Trans. I 307-314 (1982); ALMQUIST et al, J. Med. Chem., 23, 1392-1398 (1980); JENNINGS-WHITE et al, EP-45665: HOLLADAY et al, Tetrahedron Lett. 24, 4401-4404 (1983). HRUBY et al, Life Sci. 31, 189-199 (1982)).

Derivatives of the peptides according to the invention include polymers of these peptides, more preferably dimers of these peptides, via for example a thiol group of cysteine, or oligomers by grafting of peptides onto polylysines (MAP), or coupling of these peptides to carrier proteins (BSA, KLH, toxins, etc), or to lipid chains.

The peptides that are the subject of the present invention can be readily obtained by any means known to those skilled in the art, in particular via the synthetic process.

A subject of the invention is also peptides comprising a sequence SEQ ID No: 1 or peptides comprising a functional fragment of these peptides, a homolog, a chemical analogue of these peptides or a chemical derivative of these peptides. In fact, one of the terminal amino acids of the PP peptide comprises a free terminal amine function and the other comprises a free terminal carboxyl function, it being possible for each of these two functions to be involved in a peptide linkage with the C-terminal acid, respectively the N-terminal amine, of another peptide fragment. Preferably, these peptides comprise at most, 100 amino acids, preferably at most 80 amino acids, even more preferably at most 60 amino acids, and advantageously at most 40 amino acids.

The immunogenic nature of the polypeptides or peptides of the invention can be verified in various ways known to those skilled in the art. Thus, the polypeptides can be brought into contact with antibodies (or serum from infected individuals), the demonstration of antigen-antibody complexes indicating the ability of the polypeptides of the invention to carry immunogenic epitopes or fragments.

Another subject of the invention lies in proteins comprising a peptide as defined above, coupled with a carrier protein, for instance the KLH protein or the BSA protein. This coupling makes it possible to increase the immunogenicity of the peptide of the invention. Carrier proteins are illustrated in documents U.S. Pat. No. 4,608,251; U.S. Pat. No. 5,945,104 and WO 90/15878.

The coupling of the peptide of the invention and of the carrier protein can be carried out in a known manner by chemical coupling or by addition of the DNA sequence of the peptide before or after that of the carrier protein in a plasmid, and then expression and purification of the protein, that is given the name fusion protein.

Another subject of the invention concerns antibodies directed specifically against a protein, a polypeptide or a peptide according to the invention. They are preferably antileptospiral antibodies, that bind an epitope present in a protein, a polypeptide or a peptide according to the invention. The antibodies of the invention are preferably specific for leptospires, in particular pathogenic leptospires, although weaker (or non-specific) binding may be observed experimentally with other antigens.

The antibodies according to the invention can be polyclonal or monoclonal antibodies. They are generally produced by immunization of an animal with a peptide, a polypeptide or a protein according to the invention and recovery of the serum, of the milk or of the egg if birds are involved (so as to obtain the polyclonal antibodies) or of cells of the thymus or of the spleen for the production of hybridomas that produce monoclonal antibodies.

The antibodies according to the invention are more preferably antibodies that recognize the PP peptide of sequence SEQ ID No: 1 as defined above, a functional fragment thereof, a homolog, a chemical analogue or a chemical derivative thereof.

The antibodies of the invention advantageously have the ability to recognize at least two pathogenic leptospiral strains belonging to different serogroups, more preferably at least 3 pathogenic leptospiral strains, in particular belonging to different genomic species.

According to a particular embodiment, the antibodies according to the invention are polyclonal antibodies prepared by immunizing an animal with the PP peptide. The animal may be a rodent (rat, mouse, gerbil, hamster, guinea pig, etc.), a primate, a rabbit, a pig, a horse, a bovine, a bird, etc. The polyclonal antibodies are generally recovered from the serum of the immunized animals or the eggs, according to protocols known to those skilled in the art.

According to another particular embodiment, the antibodies according to the invention are monoclonal antibodies prepared from hybridomas obtained by fusion between an immortalized cell (for example a myeloma) and an antibody-producing cell taken from an animal immunized with the PP peptide as defined above. The animal may be a rodent (rat, mouse, gerbil, hamster, guinea pig, etc.), a primate, a rabbit, a pig, a horse, a bovine, a bird, etc.

The antibodies of the invention, in particular the monoclonal antibodies, may also be humanized, i.e. artificially modified so as to comprise regions of heavy or light chains of human origin.

The invention also relates to fragments or derivatives of such antibodies, for example Fab or F(ab')2 fragments, ScFvs (single-chain antibodies), etc.

As will be developed in the subsequent text, the antibodies of the invention can be used, for example, for detecting pathogenic leptospiral strains or products secreted by the same leptospires in test samples (in particular blood, milk, cerebrospinal fluid or urine samples), or for inducing (emergency) protection against leptospiral infections.

Another subject of the invention lies in any nucleic acid encoding a polypeptide, a peptide or a protein as defined above. The nucleic acids may be DNAs or RNAs, in particular recombinant, genomic, synthetic or semi-synthetic DNAs, or else mRNAs, or fragments or derivatives thereof. The nucleic acids can be obtained from libraries, cloned from leptospiral bacteria (in particular by PCR), produced by artificial synthesis using nucleic acid synthesizers, or else prepared using combinations of these methods (enzymatic digestions, legations, cloning, modifications, etc.). The nucleic acids can also be modified in order to improve codon use, to eliminate cryptic promoters, to reduce secondary structures, etc.

The invention also relates to vectors comprising a nucleic acid as defined above. This may be a vector of the type plasmid, cosmid, episome, artificial chromosome, phage, virus, etc. It is more preferably a plasmid, for example a plasmid that is replicative or a plasmid that integrates in bacteria or eukaryotic cells (yeast, mammalian cells, bird cells, insect cells, etc.) or a recombinant virus, in particular a defective virus (such as a poxvirus, an adenovirus, a retrovirus, a baculovirus, a herpesvirus, etc.).

The plasmid vectors can be prepared by conventional techniques using commercially available plasmids such as pUC, pBR, pCN, etc.

The invention also relates to any recombinant cell comprising a nucleic acid or a vector as defined above. The recombinant cell may be a bacterium (for example a strain of E. coli), or a eukaryotic cell, in particular a yeast, a mammalian cell, a bird cell or an insect cell, etc. The recombinant cells can be used in particular for producing the polypeptides of the invention, and also as models for searching for compounds capable of neutralizing or of antagonizing the activity of the PP peptide.

The invention also relates to any nonhuman transgenic organism, in particular any nonhuman mammal; any bird or any plant organism, comprising a nucleic acid as defined above in its cells. Advantageously, these transgenic organisms are obtained by homologous recombination. Such mammals (rodents, canines, rabbits, goats, pigs, etc.) and plants can in particular be used for producing the polypeptides of the invention and for identifying compounds for therapeutic or vaccine purposes, for example.

Another subject of the present invention lies in nucleotide probes and/or primers that can be used for detecting and/or amplifying leptospiral nucleic acids, and in particular for detecting the presence of a pathogenic leptospiral strain or of a product secreted by the latter, in a test sample (in particular a biological product or a product contaminated with a biological product).

The nucleotide probes according to the invention advantageously comprise a nucleic acid as defined above. They are preferably single-stranded, and can be labeled, for example by radioactive labeling, enzymatic labeling, fluorescent labeling, chemical labeling, etc. A probe according to the invention preferably comprises a sequence complementary to all or part of the nucleotide sequence SEQ ID No: 1 or one of the peptides according to the invention as defined above. The probes of the invention can be used for detecting the presence of a pathogenic leptospiral strain or of a product secreted by the latter, in any sample, in particular a biological sample. In fact, they are preferably (i) specific for the pathogenic leptospiral strains and (ii) reactive with different serovars and different genomic species of pathogenic leptospires. A preferred probe according to the invention comprises the complete sequence of the nucleotide sequence encoding PP, or a fragment thereof.

The nucleotide primers according to the invention are oligonucleotides, generally less than 40 bases long, comprising the sequence of a nucleic acid as defined above. The primers can be used for amplifying leptospiral nucleic acids, in particular for amplifying the sequence encoding PP or a part thereof, for example by PCR reaction.

The invention relates more particularly to any pair of primers that makes it possible to amplify a region of the sequence encoding PP as defined above. Preferably, the amplified region comprises at least 50 bp.

The probes, primers or oligonucleotides of the invention are preferably complementary to at least one region of the sequence encoding PP. The complementarity is generally complete, so as to provide better hybridization selectivity. However, some mismatches can be tolerated. These probes or oligonucleotides can be synthesized by any technique known to those skilled in the art, for example by cleavage from the nucleic acids described above, or by artificial synthesis, or by combining these techniques. The probes and primers are particularly useful for detecting the presence of pathogenic leptospiral strains, and/or diagnosing leptospiroses, as will be explained in detail below.

Various teams are working on improving the antigens for indirect diagnosis of leptospirosis, the aim being to produce operational methods that can be readily used in particular in non-industrialized countries, being major victims of these pathologies. The products currently proposed on the market are complex extracts of leptospiral cultures. This complexity reproduces that of the live strains used in the MAT and does not therefore provide any substantial improvement in terms of reproducibility and of practicability.

The demonstration of antibodies directed against an antigen specific for pathogenic stains is therefore particularly advantageous. The present invention can thus be used from a diagnostic, vaccine, therapeutic and/or experimental point of view.

From the point of view of indirect diagnosis, given its presence in or its secretion by the pathogenic strains, the PP peptide of the invention can be used as an antigenic unit capable of revealing antibodies produced during an infection with a pathogenic strain, irrespective of the serogroup to which it belongs. This therefore makes it possible for the experimental diagnosis of leptospirosis to be provided by many laboratories that have normal equipment (for example ELISA or dot), whereas the MAT requires live cultures to be maintained and, as a result, the standardization thereof is very difficult.

A particular subject of the invention therefore lies in the use of a polypeptide, a peptide or a protein as defined above, for detecting, in vitro, the presence of anti-leptospiral antibodies in a biological test sample (in particular a biological sample such as blood, serum, milk, urine, tissue, etc., or a non-biological sample such as water, etc.). Another subject of the invention lies in an in vitro method for detecting the presence of anti-leptospiral antibodies in a test sample, this method comprising bringing this sample (or a dilution) into contact with a polypeptide, a peptide or a protein as defined above, and demonstrating the formation of antigen-antibody complexes.

From the point of view of direct diagnosis, the antibodies (or antibody fragments or derivatives) according to the invention, in particular the monoclonal antibodies of the invention, allow direct demonstration of the pathogenic agent or of secreted products present in a test sample (such as a biological sample or another type of sample such as water). The demonstration can be carried out by any immunological method known to those skilled in the art, such as by capture ELISA, RIA, direct or sandwich assays, etc., or by immunological revelation of this peptide in pathogenic or non-pathogenic samples.

Another subject of the invention therefore lies in the use of an antibody (or antibody fragment or derivatives) according to the invention, in particular of one or more monoclonal antibodies of the invention, for detecting the presence of a pathogenic leptospiral strain or of its secreted products, in a sample, in particular a biological sample. Another subject of the invention lies in a method for detecting the presence of a pathogenic leptospiral strain or its secreted products, in a sample, comprising bringing this sample (or a dilution, or a concentration) into contact with an antibody (or antibody fragment or derivatives) according to the invention, and demonstrating the formation of antigen-antibody complexes.

For these uses, the polypeptides, peptides, proteins and antibodies can be used in soluble form, or immobilized on solid or semi-solid supports of the filter, silica, glass, plate, bead, etc. type. Use in immobilized form advantageously makes it possible to simplify the experimental detection or diagnosis of leptospirosis. These compounds can also be labeled, for example by means of fluorescent, enzymatic, biological or radioactive labels. As indicated above, the revelation of antigen-antibody complexes can also be carried out by means of a labeled additional antibody, or according to known immunological techniques (ELISA, RIA, sandwich, capture, etc.).

Another method of detection (or screening) according to the invention lies in bringing a test sample into contact with a nucleotide probe of the invention, and demonstrating hybridization between said probe and said sample. More preferably, the test sample is pretreated so as to make the nucleic acids that it contains accessible to a hybridization reaction. The treatment can consist in rupturing the cell membranes, for example by chemical treatment (detergent) and/or mechanical treatment (ultrasound, freezing-thawing, etc.). Added to this treatment may be methods for concentrating (filtration, centrifugation, etc.) the samples, in particular non-biological samples such as water samples. In a particular embodiment, the sample, in particular biological sample thus treated is subjected to an amplification reaction by means of primers of the invention, prior to the hybridization reaction with the probe. The amplification can be carried out under conventional conditions. The hybridization can be carried out on supports, on which the probe is immobilized (filters, glass, silica, etc.). The hybridization stringency conditions can be adjusted by those skilled in the art, by adapting the temperature and/or the salinity of the media.

The invention also relates to a kit for carrying out the methods of the invention comprising a probe or an oligonucleotide or a pair of primers as described above. The kits of the invention advantageously comprise the reagents suitable for an amplification and/or hybridization reaction and, optionally, a support for such reactions (filters, membranes, chips, etc.).

The present invention can also be used from a therapeutic and preventive point of view specific, although the pathogenic mode of action of the PP peptide has not yet been defined, the present application shows that it is capable of inducing protection. Administration of the antibodies directed against this peptide, whether they are of polyclonal or monoclonal origin, makes it possible, to neutralize the pathogenic impact of the leptospires in the individual in the course of progression of the disease and therefore to improve the prognosis of this disease. Similarly, administration of a polypeptide, a peptide or a protein of the invention, optionally in inactivated form, or of a corresponding nucleic acid or vector, makes it possible to induce a protective immune response against these infectious agents or their effects.

The effectiveness of the peptides of the invention in the early detection of pathogenic leptospires and the induction of immunoprotection against these same leptospires is particularly notable, in particular because the PPL protein from which they are derived does not make it possible to obtain direct immunization without involving expression in an adenovirus, and because it does not allow, either, the early and specific detection of the presence of pathogenic leptospiral strains in a human or animal organism.

In addition, it is well known to those skilled in the art that peptides are, as a general rule, weakly immunogenic.

In examples that are intended to illustrate the invention, the following notable properties of the PP peptide are illustrated:

The peptide consisting of the sequence ID No. 1 is recognized by ELISA by several monoclonal antibodies against the PPL protein, and in particular 4D4H4E5 and 6E5A2F2 (international application WO 01/59123, Example 2).

It has also been shown that the PP peptide, whether or not it is coupled to a carrier protein, is very immunogenic in the mouse, rabbit (Example 3) and gerbil (Example 7) model.

In a third step, the antibody response directed against the PP peptide was analyzed on the sera from gerbils immunized with the PPL-adenovirus. A correlation can be observed between the immune response directed against the PP peptide and the protection of the animals subsequent to immunization with PPL via the adenovirus, which supports the hypothesis that there is a protective effect associated with the sequence of this peptide (Example 6).

In a fourth step, the PP peptide was coupled to the KLH carrier protein and effective protection against a challenge was observed in gerbils immunized with PP-KLH (Example 7). The PP peptide has at least one protective epitope in its sequence. The peptide alone made it possible to induce a significant protection against a challenge (Example 7).

In a fifth step, the discriminating effectiveness of the PP peptide as an antigen for diagnosing leptospirosis was evaluated in several species (humans, dogs, bovines, horses). Whatever the species considered, the PP peptide is found to be an antigen capable of demonstrating an immune response specific for an infection with pathogenic leptospires, and in particular in the early phase (Example 4).

Finally, immunization trials showed the protective effect of the PP peptide in dogs (Example 8).

These results demonstrate that, while the lipopolysaccarhide antigens are clearly the carrier for effective protection with respect to a homologous infection, the starting point for constituting the vaccine preparations currently employed both in humans and in animals, the PP peptide, used alone, is capable of inducing cross protection between different serogroups of the species *Leptospira interrogans* ss (*Icterohaemorrhagiae, Canicola, Autumnalis*). The heterologous protection is also induced between different genomic species of the former species *Leptospira interrogans* sl (here *L. borgpetersenii* and *interrogans* ss), whereas it is absent from the former saprophyte species *Leptospira biflexa* sl.

The present invention therefore relates to the use of the PP peptide, of its natural or synthetic fragments, of its chemical derivatives whatever they are, of its homologs, or of its chemical analogs, used alone or combined with other proteins or lipopolysaccharide fractions derived from leptospires, or with adjuvants of immunity whatever their nature, for preparing a vaccine composition for veterinary or human use, in particular for preparing a composition intended to induce a protective immune response against different pathogenic leptospiral species and serovars.

A subject of the invention is also a pharmaceutical composition, in particular a vaccine, comprising a polypeptide or a nucleic acid as defined above.

A subject of the invention is also a composition comprising one or more antibodies as described above, in particular for inducing protection.

The immunogenic compositions, vaccines or antibodies of the invention can be used in injectable form or per os or in transcutaneous form, for example in combination with carriers that are acceptable from a pharmaceutical or veterinary point of view, or with adjuvants. The amounts of immunogens administered, and the frequency or the number of administrations, can be adjusted by those skilled in the art according to the individual, to the state of evolution of the injection, etc. Typically, one or two injections, 2 weeks apart, are given, with amounts suitable for the species, for example 30 µg of peptide coupled to the carrier protein according to the invention. Further injections can be envisioned, or larger amounts can be administered, in particular in the case of oral administrations.

The immunogenic or vaccine compositions of the invention have in particular the following advantages:

Effectiveness: Induction of cross protection avoiding the accumulation of different antigenic preparations of partial effectiveness in order to prevent infection with the various infecting strains present in a given country for a given species.

Innocuousness: The use of a peptide of the invention (possibly coupled to a carrier protein, or polypeptides, antibodies and nucleic acids) avoids introducing into the immunized individual many antigens that are not necessary for the protection and are therefore to say the least needless, or even dangerous in repeat uses. It is thus thought that recurring uveitis in horses (which can lead to the animal becoming blind) is induced by a post-infectious immune response due to leptospiral proteins that have a composition similar to some structural proteins of the eye of the horse. Moreover, it appears that, in humans, repeated immunizations are progressively less well-tolerated over time. In addition, no long-term pharmacovigilance data are available.

The compositions of antibodies (polyclonal, monoclonal, humanized or non-humanized) can advantageously prevent, in an emergency or passively, a serious and/or fatal progression of established leptospirosis in humans or animals.

Compatibility with prophylaxis health measures: Currently, it is impossible to differentiate post-immunization antibodies from post-infection antibodies, the production of agglutinating antibodies being obtained in both cases. This vaccine used in the major species of production (there are not currently any in France and the effectiveness of those that exist abroad is difficult to demonstrate) would make it possible to demonstrate a medical prophylaxis making it possible, despite everything, to screen for the wild-type infection and therefore allowing livestock to be labeled as unaffected, which would increase their value for exportation.

Limitation of the use of antibiotics in farming: The lack of possibilities for eradicating leptospires (maintained in the environment by many animal species of the wild-type fauna that act as reservoirs) currently makes it possible to use an antibiotic treatment extended to the entire herd when clinical problems or economic losses are recognized as being associated with leptospirosis infection. This therefore contributes to the intensive use of antibiotics in farming, which use is controversial in terms of consequences for public health.

The industrial production of such a vaccine should, finally, be simplified compared to the vaccines of the prior art since it is not necessary to modify the antigenic composition of the vaccine preparation according to the species, or according to the specific epidemiological conditions of the geographical regions where it would be applied.

The invention also relates to the polypeptides, proteins and peptides as defined above, in attenuated form, i.e. conserving the immunogenic properties and essentially lacking any other biological activity.

The invention also relates to the use of the nucleic acids or vectors as described above, for the in vitro or ex vivo production of the polypeptides, proteins and peptides of the invention, whatever the methods of genetic recombination used: transgenic animals, bacteria, eukaryotic cells, plants, plasmids, viruses, acellular culture medium extraction, etc. The techniques for producing recombinant proteins are well known to those skilled in the art and can be applied to the present invention (strong promoters, inducible promoters, termination signals, transfection techniques, etc.).

Description of the tools: Identification of a peptide (PP) for the purposes of use as a vaccine, diagnostic use and therapeutic use The present invention will be described in detail by means of the following examples, which should be considered as nonlimiting illustrations.

FIGURE LEGENDS

FIG. 1: $IgG_1$ antibody response of 5 mice immunized with the PP peptide coupled to the KLH carrier protein for a trial 1 and 2, expressed as corrected optical density as a function of dilution.

FIG. 2: $IgG_{2A}$ antibody response of 5 mice immunized with the PP peptide coupled to the KLH carrier protein for a trial 1 and 2, expressed as corrected optical density as a function of dilution.

FIG. 3: IgG antibody response of a rabbit immunized with the PP peptide, expressed as corrected optical density as a function of dilution.

FIG. 4: Comparison of the IgM and 190 antibody response, in sera originating from human patients not suffering from leptospirosis (confirmed by the MAT) but two of whom suffer from Lyme disease (serum 151358 and 153272), against the PP peptide and against the recombinant PPL protein, expressed as optical density (OD).

FIG. 5: IgM and IgG antibody response, in 5 sera originating from human patients suffering from leptospirosis, confirmed or not confirmed by the MAT, against the PP peptide expressed as optical density (OD).

FIG. 6: Compared PP and PPL response, either IgM or IgG, for sera originating from 4 SPF dogs, three of which are immunized against leptospirosis (CN V), expressed as optical density (OD).

FIG. 7: IgM and IgG antibody response, in 7 sera originating from dogs that are clinical suspects (leptospirosis confirmed by the MAT), compared with that of 3 immunized normal SPF dogs (3039, 3051, 3058), against the PP peptide, expressed as optical density (OD); Nos. 210749 and 210750 originate from the same animal, taken 4 days apart (CN=dog).

FIG. 8: IgG antibody response, in 4 bovine sera derived from livestock suspected to be suffering from leptospirosis, against the PP peptide, expressed as optical density.

FIG. 9: IgG antibody response, in 6 equine sera, against the PP peptide, expressed as optical density.

FIG. 10: Kinetics of the antibody response against the PP peptide, expressed as corrected optical density, in gerbils immunized via the adenovirus.

FIG. 11; Kinetics of the IgG antibody response against the PP peptide, expressed as corrected optical density as a function of dilution (A) or of time (B), in gerbils immunized with the PP peptide coupled to the KLH carrier protein.

FIG. 12: Survival curve for gerbils immunized with the PP peptide coupled to the KLH carrier protein and subjected to a *Leptospira interrogans* sl serovar *canicola* leptospiral challenge (CH).

FIG. 13: Survival curve for gerbils immunized with PP-KLH or PP and subjected to a *Leptospira interrogans* sl serovar *canicola* leptospiral CH.

FIG. 14: Timetable of the immunization trial with the PP peptide coupled to the KLH carrier protein in dogs, with a *Leptospira interrogans* sl serovar *canicola* leptospiral challenge.

FIG. 15: Evolution of the increase in weight of the control dogs and immunized dogs (immunized with the PP peptide coupled to the KLH carrier protein) before challenge.

FIG. 16: Evolution of the increase in temperature of the control dogs and immunized dogs (immunized with the PP peptide coupled to the KLH carrier protein) subjected to a *Leptospira interrogans* sl serovar *canicola* leptospiral challenge.

FIG. 17: Evolution in the platelet variation of control dogs and immunized dogs (immunized with the PP peptide coupled to the KLH carrier protein) subjected to a *Leptospira interrogans* sl serovar *canicola* leptospiral challenge.

FIG. 18: Quantitative evolution of the variation in white blood cells of the control dogs and immunized dogs (immunized with the PP peptide coupled to the KLH carrier protein) subjected to a *Leptospira interrogans* sl serovar *canicola* leptospiral challenge.

FIG. 19: Quantitative evolution of the variation in lymphocytes of the control dogs and immunized dogs (immunized with the PP peptide coupled to the KLH carrier protein) subjected to a *Leptospira interrogans* sl serovar *canicola* leptospiral challenge.

FIG. 20: Quantitative evolution of the variation in monocytes of the control dogs and immunized dogs (immunized with the PP peptide coupled to the KLH carrier protein) subjected to a *Leptospira interrogans* sl serovar *canicola* leptospiral challenge.

FIG. 21: Evolution of the increase in creatinine of the control dogs and immunized dogs (immunized with the PP peptide coupled to the KLH carrier protein) subjected to a *Leptospira interrogans* sl serovar *canicola* leptospiral challenge.

FIG. 22: Evolution of the increase in urea of the control, dogs and immunized dogs (immunized with the PP peptide coupled to the KLH carrier protein) subjected to a *Leptospira interrogans* sl serovar *canicola* leptospiral challenge.

FIG. 23: Evolution of the cumulative coefficient for the cultures and PCRs of the batches of control dogs and immunized dogs (immunized with the PP peptide coupled to the KLH carrier protein) subjected to a *Leptospira interrogans* sl serovar *canicola* leptospiral challenge.

TABLE LEGENDS

Table 1: MAT and EIA titer of 5 sera originating from human patients suffering from or not suffering from leptospirosis.

Table 2: Table for survival of gerbils immunized with the recombinant PPL protein with Freund's adjuvant after *canicola* challenge.

Table 3: Table for survival of gerbils immunized with the recombinant PPL protein adjuvented with alumina hydroxide and QS 21 after *canicola* challenge.

Table 4: Table for mortality of gerbils immunized with the PP peptide coupled to the KLH carrier protein after *Leptospira interrogans* sl *canicola* leptospiral challenge.

Table 5: Table for mortality of gerbils immunized with the PP peptide not coupled or coupled to the KLH carrier protein, after $10^{-2}$ *canicola* challenge.

Table 6: Statistical analysis of the immunization trials with the noncoupled or coupled PP peptide, according to the Log-rank test.

Table 7: Results of the cultures performed on the plasma, urine and kidney samples from the 6 control dogs and the 6 immunized dogs (immunized with the PP peptide coupled to the KLH carrier protein) subjected to a *Leptospira interrogans* sl serovar *canicola* leptospiral challenge.

Table 8: PCR results on the plasma, urine and kidney samples from the 6 control dogs and from the 6 immunized dogs (immunized with the PP peptide coupled to the KLH carrier protein) subjected to a *Leptospira interrogans* sl serovar leptospiral challenge.

Sequence Legends

SEQ ID No. 1: PP peptide sequence.

EXAMPLE 1

Synthesis of the PP Peptide

The PP peptide represented in the sequence SEQ ID No. 1 is a 25 amino acid peptide which corresponds to the fragment aa153-aa177 of the PPL protein of *Leptospira interrogans* al.

The peptide ID No. 1 of 25 amino acids was synthesized by neosystem.

The crude peptide is purified by HPLC.

The homogeneity of the purified peptide is verified by HPLC and the theoretical structure is confirmed by measuring the mass of this peptide by ES-MS mass spectrometry, compared with that calculated from the theoretical amino acid sequence of this peptide.

EXAMPLE 2

Identification of the PP Peptide Against Monoclonal Antibodies

The peptide ID No. 1 was used in ELISA. It was used as adsorption antigen (diagnostic protocol) with, as primary antibodies, various monoclonal antibodies directed against the PPL protein, in particular two monoclonal antibodies 6E5A2F2 and 4D4H4E5, and sera from gerbils challenged with a *Leptospira interrogans* ss serovar *canicola* challenge. The two monoclonal antibodies recognized this peptide, which demonstrates that it has one or more immunogenic epitopes of the PPL protein. Moreover, the polyclonal gerbil sera made it possible to demonstrate the presence of antibodies directed against this peptide in an early phase after infection with pathogenic leptospires in gerbils.

EXAMPLE 3

Immunogenicity of the PP Peptide 3-1 Immunogenicity of the PP Peptide Coupled to the KLH Carrier Protein Chemical Coupling to Obtain PP-KLH In this example, the peptide used corresponds to the PP peptide (SEQ ID No. 1) to which a cysteine is added at the N-terminal position. The heterobifunctional reagent, sulfo-m-maleimidobenzoyl-N-hydrosuccinimide ester (sulfo-MBS, Pierce), used allows activation of the free amine functions of the KLH carrier protein (keyhole limpet hemocyanin, Pierce), and then coupling of the peptide via reaction of the sulfhydryl group of the cysteine added at the N-terminal end of the peptide with the maleimide portion of the sulfo-MBS reagent.

Briefly, the KLH carrier protein, solubilized in water at a concentration of 10 mg/ml, is activated using the sulfo-MBS reagent diluted in coupling buffer (83 mM sodium phosphate, pH=7.2, 0.9 mM NaCl, 0.1 M EDTA) to a final concentration of 2 mg/ml. This is added at a rate of 1 mg of reagent per 10 mg of KLH, and then the entire mixture is placed in the dark at a temperature of 15 to 25° C. for 1 hour with stirring. The KLH protein is desalified on an NAPS column equilibrated with the coupling buffer. The protein is eluted using this buffer. The fractions containing the activated KLH protein are combined. For the coupling, 8.5 mg of peptide (in the above buffer at a concentration of 2 mg/ml) are added to 10 mg of KLH (concentration of the order of 5 mg/ml) in a final volume of 6 ml. The entire mixture is placed at a temperature of 15 to 25° C. in the dark for 2 hours with stirring. The conjugate is then dialyzed against a PBS buffer (20 mM sodium phosphate, pH=7.4, 130 mM NaCl): 3 successive dialyses of twice 1 hour and then overnight at 4° C. before protein assay. The preparation is then dispensed at a rate of 100 µg per eppendorf tube and frozen at −80° C.

Antibody Response Against the PP Peptide in Mice

An immunization protocol was carried out in order to evaluate the immune response against the PP peptide coupled to KLH.

A batch of 5 mice was formed. Two injections were administered subcutaneously, two weeks apart. The 1st injection consists of 10 µg of PP peptide coupled to KLH, with complete Freund's adjuvant, in a volume of 200 µl (v/v). The 2nd injection consists of 10 µg of PP peptide coupled to KLH, with incomplete Freund's adjuvant, in a volume of 200 µl (v/v). This trial was carried out twice.

In parallel, a batch of 5 mice given nothing is used as a control.

A blood sample was taken two weeks after the second injection for serological monitoring.

The anti-PP antibodies produced in the mice are titered by means of an ELISA technique either on individual serological samples or on pools of several sera. The PP antigen is adsorbed in Immulon 4 plates (Dynatech) at a rate of 500 ng of PP per well diluted in 10 mM sodium carbonate buffer, pH=9.4.

After an overnight period at 4° C., the plates are washed with PBS containing 0.2% tween$_{20}$, and then saturated with a solution of 1% BSA in TNE (50 mM Tris, 150 mM NaCl, 1 mM EDTA, pH 7.4) for 60 min at 37° C. After 3 washes with PBS tween, one hundred µl of serum diluted in TNE containing 0.1% of BSA are deposited into each cupule and incubated for 60 min at 37° C. After 5 washes, anti-mouse IgG1 or IgG$_2$A globulins coupled to peroxidase, diluted to 1/5000 in TNE buffer-0.1% BSA, are added at a rate of 100 µl per well and placed at 37° C. for 60 min. After 5 washes, the visualization is carried out by adding 100 µl per well of a buffer [citrate/ABTS] containing $H_2O_2$. After 10 min at a temperature of 15-25° C., the reaction is stopped by adding a solution of $H_2O$/DMF (v/v) containing 5% of SDS at a rate of 100 µl per cupule. The colored reaction is read in a spectrophotometer at 405 nm.

The results of the anti-PP IgG$_1$ antibody response, expressed as corrected OD, of the immunization trials 1 and 2 with the PP peptide coupled to KLH are given in FIG. 1. The corrected OD corresponds to the OD of the immunized animal minus the OD of the pool of control animals.

A great homogeneity of the anti-PP antibody response is noted in the mice. Moreover, this response is very high since the sera diluted to 1/8000 and to 1/16 000 give a corrected Or of between 0.8 and 1.2 (optimum for reading).

similar results were obtained for trial 2.

The results of the anti-PP IgG$_{2A}$ response, expressed as corrected OD, of the immunization trials 1 and 2 with the PP peptide coupled to KLH are given in FIG. 2.

A certain homogeneity of the anti-PP IgG$_{2A}$ antibody response is noted in the mice, except for mouse 5 in trial 1. Moreover, this response is high but less substantial than the anti-PP IgG1 response.

Similar results were obtained for trial 2, the antibody response being, however, less homogeneous.

In summary, immunization of mice with the PP peptide coupled to KLH induces an IgG$_1$ and IgG$_{2A}$ anti-PP response that is both high and homogeneous.

The PP peptide coupled to the KLH protein is therefore very immunogenic.

3-2 Immunogenicity of the Noncoupled PP Peptide

To test the immunogenicity of the PP peptide alone, immunization with the PP peptide in the rabbit model was carried out, with incomplete Freund's adjuvant being added to each injection.

More precisely, two injections of 400 µg of PP peptide with incomplete Freund's adjuvant (v/v) were administered in a total volume of 2 ml.

The two injections were administered subcutaneously, two weeks apart. The rabbit serum was recovered two weeks after the second injection. The anti-PP antibodies were titered on this serum.

The anti-PP antibodies were titered in the rabbit by the ELISA technique described above, with a biotinylated anti-rabbit antiglobulin (BioAtlantic) at 1/3000 and peroxidase-coupled streptavidin as visualizing agent (RPN1231, Amersham pharmacia biotech).

The results of the anti-PP IgG antibody response, expressed as corrected OD (OD at D28, therefore after the second immunization, minus the OD at D0), of the immunization trial with the PP peptide are given in FIG. 3.

The antibody response against the FP peptide is very high since a response against the PP peptide can still be detected at a dilution of 102 400. The PP peptide alone is very immunogenic.

Summary

The PP peptide, whether or not it is coupled to a carrier protein, is capable of inducing a strong serological response in various animal models. The PP peptide is therefore very immunogenic.

EXAMPLE 4

Diagnostic Use of the PP Peptide

In order to test the discriminating effectiveness of the PP peptide as an antigen for diagnosing leptospirosis, we studied sera derived from humans, and from animals of various species, that were immunized or non-immunized, and that were Buffering from or not suffering from clinical leptospirosis.

The sera were selected according to the clinical case histories but also according to their response to the reference test (MAT).

Four animal species were tested, and represent the pets or production animals most affected by leptospirosis:

dogs bovines horses pigs

ELISA Technique

The anti-PP antibodies were titered by the ELISA technique described above with peroxidase-coupled anti-globulins chosen according to the species from which the serum analyzed is derived (anti-human, anti-dog, anti-bovine, anti-horse or anti-pig (Jackson)).

The anti-PPL antibodies were titered by the same technique.

Results 4-1 Humans IgG and IgM (Ref FIG. 4)

The study was carried out on forty human sera:

10 of these sera are cases not suffering from leptospirosis but confirmed as being lyme positive.

Thirty of these sera originate from the Pasteur Institute. The MAT and EIA assays were carried out by the CNR des leptospires [National Leptospiral Reference Center] of the Pasteur Institute in Paris. The results, MAT titer and EIA titer (IgM), of five of these sera representative of the thirty are given in table 1, in only 4 of which leptospirosis was serologically confirmed by the Pasteur Institute.

In all situations, the negative control corresponds to a pool of sera from individuals in good health (before immunization) and monitored individually by MAT.

TABLE 1

MAT and EIA titer of 5 sera originating from human patients suspected of having clinical leptospirosis

| | Sera | | | | |
|---|---|---|---|---|---|
| | 1 | 2 | 21 | 24 | 27 |
| Antibodies of IgM class (EIA)* MAT** | 3200 | Negative | 3200 | 1600 | 1600 |
| L. interrogans australis | 100 | 100 | 400 | Negative | 400 |
| L. interrogans autumnalis | 100 | Negative | 50 | 50 | 100 |
| L. interrogans bataviae | Negative | Negative | Negative | 100 | 50 |
| L. interrogans canicola | 800 | Negative | 400 | 400 | 800 |
| L. interrogans castellonis | 200 | Negative | 50 | 6400 | Negative |
| L. interrogans cynopteri | 800 | Negative | 3200 | 400 | 400 |
| L. interrogans grippotyphosa | Negative | Negative | Negative | 50 | 50 |
| L. interrogans hardjo | Negative | Negative | Negative | Negative | Negative |
| L. interrogans hebdomadis | 200 | Negative | 400 | Negative | 400 |
| L. interrogans icterohaemorrhagiae | 3200 | 50 | 800 | 1/400 | 800 |
| L. interrogans panama | Negative | Negative | 50 | Negative | Negative |
| L. interrogans pomona | Negative | Negative | Negative | Negative | 50 |
| L. interrogans pyrogenes | 400 | Negative | Negative | 400 | Negative |
| L. interrogans sejroe | 100 | Negative | 200 | 50 | 800 |
| L. interrogans tarassovi | 200 | Negative | 100 | 50 | 400 |
| Leptospirosis | Serologically confirmed | Negative | Serologically confirmed | | |

*limit 400
**limit 100

Analysis of the Specificity of the IgM and IgG Antibody Responses Against the PP Peptide and Against the Recombinant PPL Protein in Human Sera not Affected by Leptospirosis In order to estimate the potential cross responses between spirochetes, serologies were, firstly, determined on eleven human sera, ten of which originate from cases of Lyme disease; the IgM and IgG antibody responses were analyzed against the PP peptide but also against the recombinant PPL protein.

The results of the IgG and IgM response directed against the PP peptide and against the recombinant PPL protein, of 3 representative sera, are given in FIG. 4 in comparison with the negative control (pool of sera negative by MAT from normal individuals).

Response Against the Recombinant PPL Protein

Given the control and serum 2, serum 153 272 from the case confirmed to be lyme-positive shows a significant IgM serological response against the recombinant PPL protein.

Moreover, a considerable IgG serological response against the recombinant protein is detected for the control, but also for the sera that are negative for leptospirosis, which does not allow discriminating serological use of PPL.

Response Against the PP Peptide

These results show that, for confirmed cases of Lyme disease that are free of leptospirosis (sera 151358 and 153272), the IgM and IgG response against the PP peptide is of the same order as that of the control (pool of sera).

Analysis of the IgM and IgG Antibody Responses Against the PP Peptide in Sera from Humans Suffering or not Suffering from Leptospirosis Secondly, in order to assess the sensitivity, the IgG and IgM response directed against the PP peptide was analyzed on thirty human sera affected by leptospirosis (originating from the Pasteur Institute).

The results of the IgG and IgM response directed against the PP peptide of 5 representative sera (see table 1) are given in FIG. 5 in comparison with the same negative control.

Dogs IgG and IgM

Immunized SPF dogs: Analysis of the Specificity of the IgM and IgG Antibody Responses Against the PP Peptide and Against the PPL Recombinant Protein in Sera from SPF Dogs Immunized or not Immunized Against Leptospirosis In a first step, serologies were determined on sera from SPF dogs immunized against leptospirosis or not immunized. The MAT test was carried out in parallel in the laboratory.

The results of the IgG and IgM response directed against the PP peptide and against the recombinant PPL protein of these sera are given in FIG. 6 in comparison with the negative control (pool of sera originating from non-immunized SPF dogs).

Response Against the Recombinant PPL Protein

Given the control (non-immunized SPF dogs), the anti-PPL IgM serological response of the immunized dogs is significantly greater.

Moreover, the high IgG serological response against the recombinant protein, of the negative control, does not make it possible to estimate the specific vaccine response.

Response Against the PP Peptide

The results of the study of the IgG and IgM antibody response directed against the PP peptide, of the immunized dogs, are given in FIG. 6. The sera from three SPF dogs immunized with various vaccines against leptospirosis (serum No.: 3039, 3051, 3058) develop an IgM response of the same order as that of the negative control (pool of sera). As regards the anti-PP IgG response, it is stronger than that of the control but remains weak since it is less than an OD of 0.25.

Unselected Dogs Suspected of Having Clinical Leptospirosis in comparison with SPF dogs: Analysis of the IgM and IgG Antibody Responses Against the PP Peptide in Sera from Unselected Dogs Suffering or not Suffering from Leptospirosis (Regardless of Whether they are Immunized or not)

The study was carried out on more than forty canine sera. The IgM and IgG antibody responses directed against the PP antigen are given for 10 dogs representative of the various cases that can be observed.

The MAT test was carried out in parallel in the laboratory. The results of these anti-PP antibody responses in these 10 canine sera are given in FIG. 7 in comparison with a negative control.

The Non-Immunized Dogs Suspected of Having Clinical Leptospirosis

The results of the study of the IgG and IgM antibody response directed against the PP peptide, of the non-immunized dogs, are given in FIG. 7A. The negative control corresponds to the serum from SPF dogs and shows no significant IgM and IgG antibody response. Sera 210749 and 210750 were taken from the same dog, 4 days apart. The MAT titer of the first sample is negative whereas the anti-PP IgM antibody response is very high (OD>0.6) and the anti-PP IgG response is beginning since an OD of 0.3 is reached at the end of clinical progression. Seroconversion is noted with the MAT (titer=160) and, in parallel, the anti-PP IgM response has decreased, to be replaced with a very high anti-PP IgG response (OD>0.9).

The PP peptide may therefore prove to be very useful for leptospirosis diagnoses, and more particularly in the early phase, since an anti-PP IgM antibody response can be detected although the MAT titer is still negative.

Serum 210845 corresponds to a dog suffering from confirmed leptospirosis. High anti-PP IgM and IgG antibody responses of the same strength can be observed.

The Immunized Dogs

The results of the study of the IgG and IgM antibody response directed against the PP peptide, of the immunized dogs, are given in FIG. 7B with the reference of the immunized SPF controls (serum No.: 3039, 3051, 3058).

Serum 211466 corresponds to a dog exhibiting clinical signs of leptospirosis; however, the MAT titer of this serum is non-significant. The anti-PP IgM antibody response is very high (OD>0.7) whereas the anti-PP IgG response is non-significant. The dog is therefore quite probably suffering from very early-phase leptospirosis. The considerable anti-PP IgM response favors the beginning of a serological response (attested to by the moderate MAT titer).

Sera 21463 and 21457 correspond to dogs exhibiting clinical signs of leptospirosis confirmed by MAT, with a longer progression period than the previous case. They exhibit a strong IgM and IgG response directed against the PP peptide.

Summary:

The PP peptide is found to be a discriminating antigen for leptospirosis infection, whether or not the dogs are immunized. The use of the PP antigen makes it possible to detect cases of leptospiroses in the early phase, the prior vaccine-related condition not preventing the diagnostic interpretation, unlike the MAT, for which the interpretation of low titers is subject to caution.

Bovines IgG

The study was carried out on thirty bovine sera.

The results of the anti-PP antibody responses in 4 bovine sera representative of the thirty analyzed are given in FIG. 8 in comparison with a negative control.

Although all the animals of bovine herds (and other ruminants and pigs) are exposed to leptospirosis infection, few animals clinically express the disease. However, the troop is subjected to the risk of infection and all the animals develop an immune response, that is sometimes difficult to detect by MAT, hence the need for group diagnosis.

The results given therefore come from animals that have not necessarily themselves aborted, but that come from herds in which leptospirosis-related abortions have been suspected since they were not associated with conventional etiologies, and which are moreover highly suspected of having leptospirosis on the basis of the overall results of the group by MAT.

The IgG response with respect of PP was studied in 30 sera from bovines originating from 7 different herds, in comparison with a control serum originating from a pool of sera from herds made up of animals that were all negative by MAT. The results of four representative sera are given in FIG. 8. Sera 1398, 1399 and 1401 are sera that are positive by MAT. Serum 4126 originates from a herd comprising animals that are positive by MAT, but is itself negative in this test, whereas the response is very strong with respect to PP.

Summary: These results confirm the advantage of the peptide as an antigen capable of demonstrating an immune response to a leptospiral infection.

Horses IgG

The results of the anti-PP antibody responses in 6 equine sera are given in FIG. 9 in comparison with a negative control.

For this species, a particular category of animals was chosen: animals suffering from uveitis. Certain forms of uveitis in the horse are associated either with a primary phase of leptospiral invasion (in which case the animal is generally positive by MAT) or a late or recurring clinical phase caused by an "auto-immunization" phenomenon. This phenomenon is thought to be explained by sensitization to a leptospiral protein similar to a leptospiral protein. This protein is thought to have an MM of 55-60 kDa and is therefore different from that of PPL, the protein that carries the PP sequence described here.

FIG. 9 gives characteristic results of 6 animals suffering from uveitis:

Sera 421 and 1992 correspond to a serological kinetics from the same animal. At the time of the first sample, the animal was negative by MAT and became positive at the time of the second sample, attesting to the fact that this uveitis could be interpreted as a sign of ongoing progressive leptospiral infection.

Animals 2077 and 6771 are slightly positive by MAT but also with respect, to PP, supporting the leptospirosis-related cause of the uveitis observed.

On the other hand, animals 3848- and 4507 develop uveitis (probably a recurrence) for which the leptospirosis-related cause cannot be confirmed by the MAT. On the other hand, these animals developed a strong response with respect to PP, supporting the leptospirosis-related cause of the uveitis.

Summary: These results confirm the advantage of the peptide as an antigen capable of demonstrating an immune response to a leptospiral infection.

Overall summary of the diagnostic use of PP: Whatever the species considered, the PP peptide is found to be an antigen capable of demonstrating an immune response to a leptospiral infection, and in particular in the early phase, since an anti-PP IgM antibody response can be detected although the MAT titer is still negative or is subject to caution in the case of immunized animals.

EXAMPLE 5

Antibody Response Against the PP Peptide of Gerbils Subjected to Adenovirus-Mediated PPL Immunization An immunization/challenge protocol made it possible to demonstrate the protection induced by a suspension of the recombinant virus Ad-ppl, which expresses the recombinant PPL protein (international application WO 01/59123, Branger C, Sonrier C, Chatrenet B, Klonjkowski B, Ruvoen-Clouet N, Aubert A, Andre-Fontaine G, Eloit M. "Identification of the hemolysis-associated protein 1 as a cross-protective immunogen of *Leptospira interrogans* by adenovirus-mediated vaccination". Infect. Immun. 2001 November; 69(11): 6831-8).

The anti-PP antibodies were titered in the gerbil by means of the ELISA technique described above, with a biotinylated anti-gerbil antiglobulin (BioAtlantic) at 1/3000 and, as visualizing agent, peroxidase-coupled streptavidin (RPN1231, Amersham pharmacia biotech).

For each batch of gerbils, the sera were combined with respect to the various sample dates D0 (before the first immunization), D21 (before the second immunization), D35 (before the challenge) and D70 (35 days after the challenge).

The results of the IgG antibody response against the PP peptide, expressed as corrected OD, are given in FIG. 10.

The adenovirus-mediated PPL protein immunization induces a significant antibody response against the PP peptide.

The anti-PP antibody response, following the first injection, appears rapidly for the group immunized with the adenovirus expressing the recombinant PPL protein. The antibody response remains stable between the 21st day and the 35th day: the second immunization did not induce any booster effect; the maximum vaccine response appears to be reached from the 21st day.

The *canicola* challenge carried out on the 35th day allows the appearance of a response against the PP peptide in the control group and causes a memory response in the group subjected to adenovirus-mediated PPL protein immunization.

An antibody response directed against the PP peptide is therefore observed following adenovirus-mediated PPL immunization, and this antibody response may have a role in the protection observed in this immunized group subjected to a *canicola* challenge.

Summary

The immunization induced a maximum anti-PP response for the stimulation induced by the dose of PPL-expressing adenovirus used. The memory-based re-initiation brought about by the challenge follows a flatter slope than the response developed by the controls. Since the PPL protein carrying the PP epitopes is secreted by pathogenic leptospires, the antigenic stimulation induced by the challenge is weaker in the animals protected by the immunization than in the controls, in which the virulent strain does not encounter any obstacle to its multiplication.

EXAMPLE 6

Immunization Trial with the Recombinant PPL Protein (Comparative)

The immunization with the recombinant PPL protein was carried out on the gerbil model in order to test the protection that can be provided by this protein. Adjuvants make it possible to increase the immuno-genicity of antigens by generally creating an inflammatory reaction which slows down the elimination of the antigen and promotes its uptake and its presentation to lymphocytes. The nature of the adjuvant will direct the production of cytokines that promote the development of a cell-mediated or humoral response.

Three adjuvants were tested: firstly, Freund's adjuvant in experiment 1 and, secondly, QS 21 (saponin) with aluminum hydroxide in experiment 2.

Trial 1: Freund's Adjuvant

The immunization with the recombinant PPL protein was carried out in the gerbil model and followed by a challenge with *canicola* at 100 TU diluted to $10^{-1}$ (batches 1 and 2) and to $10^{-2}$ (batches 3 and 4).

The results of this experiment (survival rate) are given in table 2.

TABLE 2

Table for survival of gerbils immunized with the recombinant PPL protein with Freund's adjuvant after canicola challenge

| | $10^{-1}$ challenge | | $10^{-2}$ challenge | |
|---|---|---|---|---|
| | Batch 1 (PPL) Dead/alive | Batch 2 control Dead/alive | Batch 3 (PPL) Dead/alive | Batch 4 control Dead/alive |
| Jul. 09, 1999 | 1/10 | 0/15 | 0/10 | 0/15 |
| Challenge: Can, d0 | 0/9 | 0/15 | 0/10 | 0/15 |
| D11 | 4/5 | 8/7 | 0/10 | 0/15 |
| D12 | 4/1 | 4/3 | 1/9 | 1/8 |
| D13 | 1/0 | 1/2 | 3/6 | 7/7 |
| D14 | 0/0 | 0/2 | 2/4 | 1/6 |
| D15 | 0/0 | 0/2 | 1/3 | 4/2 |
| D16 | 0/0 | 0/2 | 0/3 | 0/2 |
| D30 | 0/0 | 0/2 | 0/3 | 0/2 |
| Alive/number* | 0/10 | 2/15 | 3/10 | 2/15 |

Letters in BOLD: beginning of gerbil mortality for each batch
*number considered from the D0 challenge The mortality rate of the batch immunized with the recombinant PPL protein in the presence of Freund's adjuvant, whatever the challenge considered, is similar to that of the corresponding control batches.

The mortality of the batches subjected to the same challenge begins at the same time: 11th and 12th day for, respectively, the challenges with 100 TU diluted to $10^{-1}$ and $10^{-2}$.

This trial did not make it possible to demonstrate significant protection induced by immunization with the recombinant PPL protein after a *canicola* challenge.

Trial 2: Adjuvant Alumina Hydroxide and QS 21

The immunization trial with the recombinant PPL protein was carried out again under the same conditions; however, the protein was adjuvented with QS 21 and alumina hydroxide.

The immunization of gerbils with the recombinant PPL protein adjuvented with QS 21 and alumina hydroxide was followed by a *canicola* challenge. The results are given in table 3.

TABLE 3

Table for survival of gerbils immunized with the recombinant PPL protein adjuvented with alumina hydroxide and QS 21 after canicola challenge

| | Batch immunized with PPL Dead/alive | Control batch Dead/alive |
|---|---|---|
| Apr. 06, 2000 | 1/15 | 0/15 |
| Challenge: Can, D0 Apr. 19, 2000 | 0/14 | 0/15 |
| D8 | 1/13 | 2/13 |
| D9 | 4/9 | 2/11 |
| D10 | 0/9 | 2/9 |
| D11 | 2/7 | 0/9 |
| D12 | 0/7 | 0/9 |
| D13 | 0/7 | 0/9 |
| D30 | 0/7 | 0/9 |
| Alive/number* | 7/14 | 9/15 |

Letters in BOLD: beginning of gerbil mortality for each batch
*number considered from the D0 challenge The survival rates for the batch immunized with the adjuvented recombinant PPL protein and the control batch are similar. The gerbil mortality of the two batches begins on the same day: the 8th day.

We were unable to demonstrate any significant protection provided by the recombinant PPL protein, whether in the presence of Freund's adjuvant or alumina hydroxide coupled with QS 21.

Therefore, whatever the adjuvant used, no significant protection subsequent to immunization with the recombinant PPL protein could be demonstrated. Now, an immunization/challenge protocol has made it possible to demonstrate the protection induced by suspension of the recombinant virus Ad-ppl, which expresses the recombinant PPL protein (patent WO 01/59123, Branger et al., 2001). It therefore appears to be essential to determine the epitope(s) of the PPL protein that is (are) responsible for the protective effect observed.

With this aim, the protective effect of the PP peptide was compared with that obtained with PPL.

EXAMPLE 7

Immunization Trial with the PP Peptide Coupled or not Coupled to the KLH Carrier Protein The aim of the immunization with the PP peptide in the gerbil model is to evaluate both the antigenicity of the chosen sequence by means of the antibody response and the possible protection provided by this peptide.

Trial 1: Protocol for Immunization of Gerbils with the PP Peptide Coupled to the KLH Carrier Protein An immunization/challenge protocol was carried out in order to evaluate the protection that can be provided by the PP peptide (SEQ ID No. 1) coupled to the KLH protein.

This construct is administered subcutaneously without adjuvant, with PBS as a negative control (batch 2).

Batch 1: 10 gerbils, 2 injections of 30 μg of PP-KLH in 300 μl, subcutaneously.

Batch 2: 10 gerbils, 2 injections of PBS in 300 μl.

The two injections in a volume of 300 μl were administered subcutaneously, two weeks apart. A challenge by intraperitoneal injection of 0.5 ml of a $canicola$ culture with a titer of 90 to 100 TU (turbidimetry) diluted to $10^{-2.5}$ was administered two weeks after the second injection.

Antigenic response: Monitoring by ELISA of the immune response of the gerbils against the PP peptide The anti-PP antibodies were titered in the gerbil by means of an ELISA technique (described above) with a biotinylated anti-gerbil antiglobulin (BioAtlantic) at 1/3000 and, as visualizing agent, peroxidase-coupled streptavidin (RPN1231, Amersham pharmacia biotech).

For each batch of gerbils, the sera were combined with respect to the various sample dates D0 (before the first immunization), D14 (before the second immunization) and D28 (before the challenge).

The results of the IgG antibody response against the PP peptide, expressed as corrected OD (OD of the treated sera corrected with respect to the OD of the control sera), are given in FIG. 11.

The immunization with the PP peptide coupled to KLH induces a significant antibody response against the PP peptide. The anti-PP antibody response, following the first injection, is very high since the sera diluted to 1/6400 and to 1/12 800 (FIG. 11, A) give a corrected OD of between 0.8 and 1.2 (optimum for reading). A clear boost effect is caused by the second injection, since the corrected OD obtained at D28 is more than double that obtained at D14 for the three dilutions observed (FIG. 11, B).

Conclusion:

The antigenicity of the peptide chosen is considerable.

Protection Against Challenge

The results of this trial in terms of mortality rate and survival curve are given, respectively, in table 4 and FIG. 12.

TABLE 4

Table for mortality of gerbils immunized with the PP peptide coupled to the KLH carrier protein after $10^{-2.5}$ canicola challenge

| Date | Batch 1 PP-KLH | Batch 2 PBS |
|---|---|---|
| Before challenge | 10 | 10 |
| Challenge* | 10 | 10 |
| D4 | 10 | 10 |
| D5 | 10 | 10 |
| D6 | 7 | 5 |
| D7 | 5 | 3 |
| D8 | 4 | 0 |
| D9 | 4 | 0 |
| D10 | 4 | 0 |
| D11 | 4 | 0 |
| D30 | 4 | 0 |
| Mortality rate | 6/10 | 10/10 |
| Survival rate | 4/10 | 0/10 |

The mortality of batch 2 corresponding to the control group that received PBS (0/10) is very high since, at D8, no gerbil has survived an $L.\ interrogans$ serovar $canicola$ challenge. This challenge is severe since, firstly, the LD100 was reached in 8 days and, secondly, the mortality began early, from the 5th day, and was very rapid since all the controls died within 3 days. On the other hand, it is noted that 4 of the 10 animals of the batch of gerbils immunized with the PP peptide coupled to the KLH protein survived definitively (monitoring for four weeks after challenge).

This experiment does not make it possible to demonstrate, at the usual risk of 0.05, significant protection induced by the PP peptide against a $10^{-2.5}$ $canicola$ challenge. However, this protection exists for a risk $p < 0.07$ (log-rank test).

Trial 2: Protocol for Immunization of Gerbils with the PP Peptide Coupled or not Coupled to the KLH Carrier Protein The experiment consisting of immunization with the PP peptide coupled to the KLH carrier protein was carried out again under similar conditions in order to validate the results obtained in trial 1. However, it appeared to us to be interesting to also reproduce this trial with the non-coupled peptide, given the strong antigenicity of the PP peptide demonstrated in trial 1.

An immunization/challenge trial was carried out in order to evaluate the protection that can be provided by the PP peptide (SEQ ID No. 1) coupled or not coupled to the KLH protein.

This construct is administered subcutaneously without adjuvant, and PBS is administered by the same route as the negative control (batch 3).

Batch 1: 12 gerbils, 2 injections of 30 μg of PP-KLH in 300 μl.
Batch 2: 12 gerbils, 2 injections of 30 μg of PP in 300 μl.
Batch 3: 15 gerbils, 2 injections of PBS in 300 μl.

The two injections in a volume of 300 μl were administered subcutaneously, two weeks apart. A challenge by intraperitoneal injection of 0.5 ml of a serovar $canicola$ leptospiral culture with a titer of 90 to 100 TU (turbidimetry) diluted to $10^{-2}$ was administered three weeks after the second injection.

The results of this trial in terms of mortality rate and survival curve are given respectively in table 5 and FIG. 13:

TABLE 5

Table for mortality of gerbils immunized with the PP peptide coupled or not coupled to the KLH carrier protein after $10^{-2}$ canicola challenge

|  | Batch 1 PP-KLH | Batch 2 PP | Batch 3 Control (PBS) |
|---|---|---|---|
| Challenge; Can, D0 | 12 | 12 | 15 |
| D4 | 0/12 | 0/12 | 0/15 |
| D5 | 0/12 | 0/12 | 0/15 |
| D6 | 0/12 | 0/12 | 1/15 |
| D7 | 0/12 | 0/12 | 4/14 |
| D8 | 0/12 | 2/12 | 1/10 |
| D9 | 1/12 | 2/10 | 1/9 |
| D10 | 0/11 | 0/8 | 0/8 |
| D11 | 0/11 | 0/8 | 0/8 |
| D12 | 0/11 | 0/8 | 0/7 |
| D13 | 0/11 | 0/8 | 0/7 |
| D14 | 0/11 | 0/8 | 0/7 |
| D15 | 0/11 | 0/8 | 0/7 |
| D16 | 0/11 | 0/8 | 0/7 |
| D17 | 0/11 | 0/8 | 0/7 |
| D28 | 0/11 | 0/8 | 0.7 |
| Mortality rate | 8.3 | 33.3 | 53.3 |
| Survival rate | 91.6 | 66.7 | 46.7 |

The mortality of batch 3, the control group having received PBS, is the highest of all the batches and corresponds to the lethal dose 50 (7/15). The mortality in the controls began early, from D6, whereas it only begins at DB for the batch immunized with PP and D9 for the batch immunized with PP-KLH.

The mortality in the group immunized with PP-KLH, following an L. interrogans serovar canicola challenge, is the lowest (1/12) and the latest (D9), whereas that of the batch immunized with PP is 4/12 and begins at D8.

Although the protection observed with the peptide coupled to the KLH carrier protein is more effective, this experiment makes it possible to demonstrate a protective effect induced by the PP peptide, coupled or not coupled to the KLH carrier protein, against a $10^{-2}$ serovar canicola leptospiral challenge at a probability p<0.02 (log-rank test).

The survival rate observed for the batch immunized with PP-KLH subcutaneously confirms the results observed in the first experiment (trial 1). Moreover, the result of trial 1 following immunization with the PP peptide confirms the strong immunogenicity of this peptide and demonstrates its protective effect.

Statistical Analysis of the Results of the Two Experiments

TABLE 6

Statistical analysis of the immunization trials with the coupled or noncoupled PP peptide according to the log-rank test

|  | Experiment 1 | | Experiment 2 | | Accumulation of the two trials | |
|---|---|---|---|---|---|---|
|  | $\chi^2$ | p | $\chi^2$ | p | $\chi^2$ | p |
| PP-KLH/control | | <$7.10^{-2}$ | 6.84 | <$1.10^{-2}$ | 10.1 | <$2.10^{-3}$ |
| PP/control | — | — | 5.64 | <$2.10^{-2}$ | — | — |

The PP peptide coupled to the KLH carrier protein provides significant protection against a canicola challenge for the two experiments. This protection is significant with respect to the survival of the animals estimated by means of the log-rank test, whatever the experiment; the combination of the two experiments increases the significance of the experiment, whether this is with the $\chi^2$ test or the log-rank test.

Summary

The immunization with the PP peptide coupled or not coupled to the KLH protein made it possible to demonstrate the protective effect of the PP peptide, on two occasions, following a challenge (canicola).

EXAMPLE 8

Immunization Trial with the PP Peptide $NH_2$— Coupled to the KLH Carrier Protein in Dogs The aim of immunizing dogs with the PP peptide is to evaluate the protective effect provided by this peptide. The protection will be studied in two parts: clinical protection, but also protection against being a renal carrier.

Protocol for Immunizing Dogs with the PP Peptide Coupled to the KLH Carrier Protein An immunization/challenge protocol was carried out in order to evaluate the protection that can be provided by the PP peptide (SEQ ID No. 1) $NH_2$-coupled to the KLH carrier protein (FIG. 14).

This construct is administered subcutaneously without adjuvant, with PBS as a negative control (batch 2).

Batch 1: 6 SPF dogs, 2 injections of 250 μg of PP-KLH in 1 ml subcutaneously.

Batch 2: 6 SPF dogs, control.

The two injections were administered subcutaneously, 18 days apart.

The challenge (CH) was carried out on $D_0$.

The animals are given a challenge at a rate of one virulent culture of 4 to 6 days. For an immunized batch and a control batch, each animal received, in each eye, 0.3 ml of the culture having a titer of 120 TU (i.e. $2 \times 10^8$ leptospires per ml) and, intraperitoneally, 4 ml of the same culture diluted ten-fold.

Summary of Results

Immunization Phase

The immunization phase was carried out from $D_{-39}$ to $D_{-1}$, ($D_0$ being the day of challenge), with the first injection on $D_{-35}$ and second on $D_{-18}$.

There was complete tolerance.

During this phase, the weight was measured on $D_{-39}$, $D_{-35}$, $D_{-28}$, and $D_{-7}$ (FIG. 15).

The evolution of the mean increase in weights between $D_{-35}$ and $D_{-7}$, is not significantly different between the control dogs and immunized dogs (p=0.8509), but there is significant evolution in weight over time (p<0.0001).

Challenge Phase

The challenge phase was carried out from $D_{-1}$ to $D_{-41}$, with the challenge on $D_0$.

During this phase, the temperature was measured on $D_0$, $D_1$, $D_2$, $D_3$, $D_4$, $D_5$, $D_6$ and $D_7$.

The hematological parameters were measured on $D_{-1}$, $D_3$, $D_7$, $D_{10}$, $D_{14}$, $D_{15}$ and $D_{41}$.

The biochemical parameters were measured on $D_{-1}$, $D_3$, $D_7$, $D_{10}$, $D_{14}$, $D_{18}$, $D_{25}$ and $D_{41}$.

Survival

No mortality was noted following the challenge

Evolution of Temperature

The evolution of the mean variation in temperature between $D_1$ and $D_7$ is represented in FIG. 16. The evolution of the mean increase in temperature between $D_0$ and $D_7$ is not significantly different between the control dogs and immunized dogs (P=0.7944). However, here and there, there is a significant difference between the control dogs and immunized dogs, at D3 and D4 (p c 0.05). The control dogs develop a more pronounced febrile peak.

Evolution of Hematological Parameters:

Platelets

Since the means for the platelets are significantly different at $D_{-1}$, the value at $D_{-1}$ is included in the analytical model.

The evolution of the mean variation in platelets between $D_{-1}$ and $D_{41}$ is represented in FIG. 17. The evolution of the mean variation in platelets between $D_{-1}$ and $D_{41}$ is significantly different between the control dogs and immunized dogs (p=0.0412). The evolution is significant over time (p=0.0003).

The thrombocytopenia is significantly more pronounced in the controls than in the immunized dogs.

Evolution of White Blood Cells

The overall evolution of the white blood cells between $D_{-1}$ and $D_{41}$ is represented in FIG. 18.

The evolution of the white blood cells between $D_{-1}$ and $D_{41}$ is not significantly different between the control dogs and immunized dogs (P=0.4407).

However, the transient leukopenia preceding leukocytosis (a conventional phenomenon in leptospirosis) is significantly greater in the control than in the immunized dogs at $D_4$ (p<0.05).

The evolution in the leukocyte composition was also analyzed.

This evolution was studied by counting with respect to leukocyte class, the count being estimated with respect to the blood composition and related to the count.

Lymphocytes

The evolution of the lymphocytes between $D_{-1}$ and $D_{41}$ is represented in FIG. 19. Significant lymphopenia is noted at $D_4$ in the controls, but is not noted at all in the vaccinated dogs, in which only the post-infectious lymphoproliferation is observed.

Monocytes

The evolution of the monocytes between $D_{-1}$ and $D_{41}$ is represented in FIG. 20. Monocyte depletion is observed early at $D_4$ only in the controls (p=0.05).

Biochemical Parameters

The heterogeneity of the reaction of the individuals in the control batch does not make it possible to objectify any protection against an acute effect in the kidneys for the two biochemical parameters: creatinine and urea levels in the blood, represented respectively in FIGS. 21 and 22.

While no significant difference can be demonstrated over the entire period monitored, two different periods are noted:

period of acute effect in the kidneys ($D_0$-$D_{10}$): no significant difference between controls and vaccinated dogs despite a tendency (p<0.15) for greater expression in the controls (higher urea level);

period of kidney colonization ($D_{10}$-$D_{41}$): during this period, the urea level in the controls remains significantly (p<0.02) higher.

Bacteriological Results

The presence of leptospires was studied jointly by PCR (PCR specific for pathogenic leptospires) and by culturing, in the urine at $D_0$, $D_{10}$, $D_{14}$, $D_{18}$, $D_{25}$ and $D_{41}$ and in the kidney samples from each animal at the end of the trial at $D_{41}$. The PCR results are given in Table 8.

Moreover, the bacteriological results were quantified through the setting up of a coefficient:

by immediate culturing. A single live leptospire can give a positive culture. A relative estimation of the bacterial concentration is expressed by means of a coefficient of 3 when a culture has developed in the third serial dilution prepared from the sample.

by PCR on frozen samples. A positive PCR does not prejudge the viability of the bacteria revealed and, moreover, a PCR is only positive for $10^2$ leptospires present. A coefficient of 1 was assigned to a PCR with a weak signal and a coefficient of 2 to a strongly positive PCR.

The overall coefficient corresponds to the sum of the grading for each dog, related to the maximum grading that all the dogs would have obtained. These results are expressed in FIG. 23.

As regards septicemia, complete agreement between the two tests at $D_3$ is noted (FIG. 23 and Tables 7 and 8). All the animals therefore still have the challenge strain at this state.

As regards kidney colonization, for the two batches, it is advisable to separate the final results obtained from the kidneys (July 3) from those obtained from the urine.

At the time of euthanasia, the two groups are renal carriers, this carrier aspect being detected both by culturing and by PCR.

However, as regards excretion in the urine per se, a considerable difference is noted in the evolution, during the challenge period, of the coefficients, obtained both for the cultures and for the PCRs.

The excretion of leptospires in the urine, reflecting renal colonization, becomes apparent later, or at a lower level in the immunized dogs (Table 7 and 8, FIG. 23). It should be noted that kidney culture is a very sensitive detection method and does not allow the semi-quantification that was done for culture and PCR.

OVERALL CONCLUSION

In the course of this trial, we demonstrated that immunization with PP (SEQ ID No. 1) coupled to a carrier protein makes it possible to induce protection against a *canicola* challenge in dogs.

More particularly, we observed:

a significant limitation of general disturbances (behavior and febrile syndrome) in the immunized dogs compared with the control dogs;

a significant limitation of hematological, platelet and leukocyte, in particular, impairments in the immunized dogs compared with the control dogs;

a limitation of affect on the kidneys with this *canicola* strain, the renal tropism of which is marked, objectified by:

From a functional point of view: the urea and creatinine levels are lower in the vaccinated dogs during the septicemia phase than those observed in the controls.

The renal colonization detected later in the immunized dogs than in the control dogs corresponds to a colonization with a lower background level or a later colonization. Now, the fact that a significant increase in urea is noted simultaneously in the control dogs favors a lower level of colonization in the immunized dogs.

TABLE 7

Results of the cultures performed on the plasma, urine and kidney samples from the 6 control dogs and from the 6 immunized dogs (immunized with PP peptide coupled to the KLH carrier protein) subjected to a Leptospira interrogans s1 serovar canicola leptospiral challenge

|  | Date | Immunized | Control |
|---|---|---|---|
| Plasma | $D_0$ | 0/6 | 0/6 |
|  | $D_3$ | 6/6 | 6/6 |
|  | $D_7$ | 0/6 | 0/6 |
| Urine | $D_7$ | 3/6 | 6/6 |
|  | $D_{14}$ | 2/6 | 4/6 |
|  | $D_{18}$ | 3/6 | 5/6 |
|  | $D_{25}$ | 4/6 | 6/6 |
| Kidneys | $D_{41}$ | 5/6 | 4/5 |

TABLE 8

PCR results on the plasma, urine and kidney samples from the 6 control dogs and from the 6 immunized dogs (immunized with PP peptide coupled to the KLH carrier protein) subjected to a Leptospira interrogans s1 serovar canicola leptospiral challenge

|  | Date | Immunized | Control |
|---|---|---|---|
| Plasma | $D_0$ | 0/6 | 0/6 |
|  | $D_3$ | 6/6 | 6/6 |
|  | $D_7$ | 0/6 | 0/6 |
| Urine | $D_{14}$ | 2/6 | 3/6 |
|  | $D_{18}$ | 1/6 | 6/6 |
|  | $D_{25}$ | 3/6 | 4/6 |
|  | $D_{41}$ | 4/6 | 4/6 |
| Kidneys | $D_{41}$ | 1/6 | 2/6 |

The invention claimed is:

1. A compound characterized in that it consists of a peptide chosen from:
   a peptide consisting of the sequence SEQ ID NO: 1 below:
   SEQ ID No: 1 Lys-Ala-Lys-Pro-Val-Gln-Lys-Leu-Asp-Asp-Asp-Asp-Asp-Gly-Asp-Asp-Thr-Tyr-Lys-Glu-Glu-Arg-His-Asn-Lys
   and
   a peptide consisting of the sequence SEQ ID NO: 1 plus an additional N-terminal cysteine residue.

2. A compound consisting of a peptide coupled to a single carrier protein, wherein said peptide is selected from the group consisting of:
   a peptide consisting of the sequence SEQ ID NO: 1 below:
   SEQ ID No: 1 Lys-Ala-Lys-Pro-Val-Gln-Lys-Leu-Asp-Asp-Asp-Asp-Asp-Gly-Asp-Asp-Thr-Tyr-Lys-Glu-Glu-Arg-His-Asn-Lys
   and
   a peptide consisting of the sequence SEQ ID NO: 1 plus an additional N-terminal cysteine residue;
   wherein said compound does not consist of the PPL protein.

3. A pharmaceutical composition comprising a peptide and a pharmaceutically acceptable carrier, wherein said peptide is selected from the group consisting of:
   a peptide consisting of the sequence SEQ ID NO: 1 below:
   SEQ ID No: 1 Lys-Ala-Lys-Pro-Val-Gln-Lys-Leu-Asp-Asp-Asp-Asp-Asp-Gly-Asp-Asp-Thr-Tyr-Lys-Glu-Glu-Arg-His-Asn-Lys
   and
   a peptide consisting of the sequence SEQ ID NO: 1 plus an additional N-terminal cysteine residue.

4. The composition as claimed in claim 3, wherein it is a vaccine.

---

SEQUENCE LISTING

<160> NUMBER OF SEQ ID NOS: 2

<210> SEQ ID NO 1
<211> LENGTH: 25
<212> TYPE: PRT
<213> ORGANISM: Leptospira interrogans sl.

<400> SEQUENCE: 1

Lys Ala Lys Pro Val Gln Lys Leu Asp Asp Asp Asp Asp Gly Asp Asp
1               5                   10                  15

Thr Tyr Lys Glu Glu Arg His Asn Lys
            20                  25

<210> SEQ ID NO 2
<211> LENGTH: 16
<212> TYPE: PRT
<213> ORGANISM: Leptospirosis

<400> SEQUENCE: 2

Thr Phe Leu Pro Tyr Gly Ser Val Ile Asn Tyr Tyr Gly Tyr Val Lys
1               5                   10                  15

5. A compound comprising a pharmaceutically acceptable salt of a peptide, wherein said peptide is selected from the group consisting of:
- a peptide consisting of the sequence SEQ ID NO: 1 below:
  SEQ ID No: 1 Lys-Ala-Lys-Pro-Val-Gln-Lys-Leu-Asp-Asp-Asp-Asp-Gly-Asp-Asp-Thr-Tyr-Lys-Glu-Glu-Arg-His-Asn-Lys
  and
- a peptide consisting of the sequence SEQ ID NO: 1 plus an additional N-terminal cysteine residue.

6. A compound according to claim 2, wherein said peptide is coupled to said carrier protein by one of the following means:
- chemically coupling said peptide to said carrier protein; or
- by the addition of a DNA coding sequence of said peptide before or after a DNA coding sequence of said carrier protein and expressing and purifying the resulting fusion protein.

7. A compound according to claim 2, wherein said single carrier protein is selected from the group consisting of: the keyhole limpet hemocyanin (KLH) protein and the bovine serum albumin (BSA) protein.

* * * * *